United States Patent [19]

Cross et al.

[11] Patent Number: 5,302,595
[45] Date of Patent: Apr. 12, 1994

[54] MUSCARINIC RECEPTOR ANTAGONISTS

[75] Inventors: Peter E. Cross, Canterbury; Alexander R. MacKenzie, Deal, both of England

[73] Assignee: Pfizer Inc., New York, N.Y.

[21] Appl. No.: 2,498

[22] Filed: Jan. 6, 1993

Related U.S. Application Data

[63] Continuation of Ser. No. 416,894, Oct. 4, 1989, Pat. No. 5,219,871.

[30] Foreign Application Priority Data

Oct. 4, 1988 [GB] United Kingdom ............ 8823203.8

[51] Int. Cl.$^5$ .................. A61K 31/495; A61K 31/44; C07D 241/02; C07D 333/36
[52] U.S. Cl. .................................. 514/255; 514/351; 514/357; 514/438; 514/445; 514/413; 514/450; 514/437; 514/454; 514/618; 514/619; 514/620; 544/336; 544/408; 546/300; 546/334; 549/65; 549/76; 549/12; 549/26; 549/354; 549/388; 564/161; 564/162; 564/164; 564/165
[58] Field of Search ............. 544/408, 336; 514/255, 514/351, 357, 445, 438, 413, 450, 437, 454, 618, 619, 620; 546/300, 334; 549/65, 76, 12, 354, 26, 388; 564/162, 164, 165, 161

[56] References Cited

U.S. PATENT DOCUMENTS 4,335,122  6/1982  McFadden et al. ............... 424/244

FOREIGN PATENT DOCUMENTS

| A75526/87 | 7/1987 | Australia | 424/244 |
| 795330 | 10/1968 | Canada | 424/244 |
| 0187509 | 7/1986 | European Pat. Off. | 424/244 |
| 0231003 | 8/1987 | European Pat. Off. | 514/357 |
| 0253327 | 1/1988 | European Pat. Off. | 514/357 |
| 0271013 | 6/1988 | European Pat. Off. | 424/244 |
| 1158083 | 12/1962 | Fed. Rep. of Germany | 514/357 |
| 87104753 | 6/1988 | Japan | 564/162 |
| 1129955 | 10/1968 | United Kingdom | 514/357 |

OTHER PUBLICATIONS

Chemical Abstracts, 70(19), p. 293, abstract no. 87390u (May 12, 1969).
Casy et al., *J. Pharm. and Pharmacol*, 19, 17-24 (1967).
Gulatieri et al., *J. Med. Chem.*, 28, 1621-28 (1985).
Maffett et al., "α,α-Diphenyl-Y-Amino Amides," 4451-7, 79 (1957).

*Primary Examiner*—Mary C. Lee
*Assistant Examiner*—Joseph K. McKane
*Attorney, Agent, or Firm*—Peter C. Richardson; Paul H. Ginsberg; Garth Butterfield

[57] ABSTRACT

Compounds of the formula I

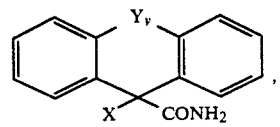

wherein X, Y and v are as defined below, novel intermediates used in their synthesis, and the pharmaceutically acceptable salts of such compounds and intermediates. The compounds of formula I and the novel intermediates used in their synthesis are muscarinic receptor antagonists that are selected for smooth muscle muscarinic sites and are useful in the prevention and treatment of diseases associated with altered motility or tone of smooth muscle, such as irritable bowel syndrome, diverticular disease, urinary incontinence, aesophageal achalasia, and chronic obstructive airways disease.

12 Claims, No Drawings

MUSCARINIC RECEPTOR ANTAGONISTS

This is a continuation, of application Ser. No. 416,894, filed on Oct. 4, 1989 now U.S. Pat. No. 5,219,871.

BACKGROUND OF THE INVENTION

This invention relates to certain amides and to novel intermediates used in their synthesis. The compounds of the invention are muscarinic receptor antagonists which are selective for smooth muscle muscarinic sites over cardiac muscarinic sites and do not have any significant antihistaminic activity. Thus the compounds are useful in the treatment of diseases associated with altered motility and/or tone of smooth muscle which can, for example, be found in the gut, trachea and bladder. Such diseases include irritable bowel syndrome, diverticular disease, urinary incontinence, oesophageal achalasia and chronic obstructive airways disease.

SUMMARY OF THE INVENTION

According to the invention there are provided compounds of the formula:

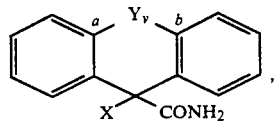

I and their pharmaceutically-acceptable salts, wherein
v is 0 or 1, with the proviso that when v is 0 there is no bond between the carbons at positions a and b;
Y is $CH_2CH_2$—, —CH=CH—, —$CH_2$—S—, —$CH_2$—O—, —O— or S; and
X is a group of the formula:

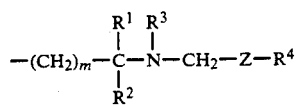

wherein
m is 1 or 2;
$R^1$ and $R^2$ are each independently H or $C_1$-$C_4$ alkyl or together represent —$(CH_2)_n$— where n is an integer of from 2 to 5;
$R^3$ is H or $C_1$-$C_4$ alkyl;
Z is a direct link, —$CH_2$—, —$(CH_2)_2$—, —$CH_2O$— or —$CH_2S$—; and
$R^4$ is pyridyl, pyrazinyl, thienyl or a group of the formula:

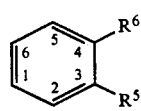

wherein
either $R^5$ and $R^6$ are each independently selected from H, $C_1$-$C_4$ alkyl, $C_1$-$C_4$ alkoxy, halo, —$CF_3$, —CN, —$(CH_2)_pNR^7R^8$, —$OCO(C_1$-$C_4$ alkyl), —$CO(C_1$-$C_4$ alkyl), —CH(OH)($C_1$-$C_4$ alkyl), —C(OH)($C_1$-$C_4$ alkyl)$_2$, —$SO_2NH_2$, —$NHSO_2(C_1$-$C_4$ alkyl), —$(CH_2)_p$OH, —$(CH_2)_p$COO($C_1$-$C_4$ alkyl), —$(CH_2)_p$CONR$^7$R$^8$, or $R^5$ and $R^6$ together represent —$(CH_2)_q$—, —$O(CH_2)_r$O— or —$O(CH_2)_r$— where in the latter the oxygen atom is attached to the 3- or 4-position of the benzene ring;
$R^7$ and $R^8$ are each independently H or $C_1$-$C_4$ alkyl;
p is 0, 1 or 2;
q is 3, 4 or 5;
r is 1, 2 or 3; and
t is 2, 3 or 4.

"Halo" means F, Cl, Br or I. Alkyl and alkoxy groups of 3 or 4 carbon atoms can be straight or branched chain. The preferred alkyl and alkoxy groups are methyl, ethyl, methoxy and ethoxy.

The preferred compounds are those wherein v is 0.
$R^1$ and $R^2$ are preferably both H or both $CH_3$.
$R^3$ is preferably $CH_3$.
Y is preferably —$CH_2CH_2$—.
In one embodiment, Z is a direct link, —$CH_2$—, —$CH_2O$— or —$CH_2S$—.
Z is preferably a direct link, $CH_2$ or $(CH_2)_2$.
$R^4$ is preferably pyridyl, or a group of the formula:

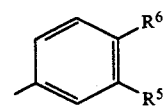

wherein either one of $R^5$ and $R^6$ is H and the other is H, $C_1$-$C_4$ alkyl, hydroxy, $C_1$-$C_4$ alkoxy, hydroxymethyl, halo, cyano, carbamoyl, carbamoylmethyl, sulphamoyl, $C_1$-$C_4$ alkanesulphonamido, ($C_1$-$C_4$ alkoxycarbonyl)-methyl, or aminomethyl, or $R^5$ and $R^6$ together represent —$(CH_2)_3$—, —$OCH_2O$—, —$O(CH_2)_2O$— or —$O(CH_2)_2$—.

$R^4$ is most preferably a group of the formula:

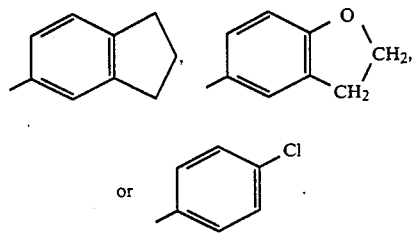

Some specific preferred compounds are those having the following formulae:

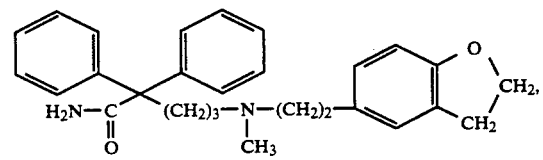

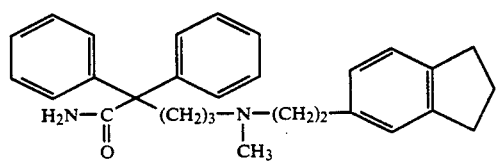

and

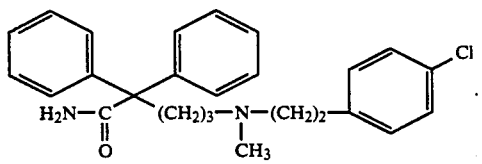

The present invention also relates to compounds having the formula

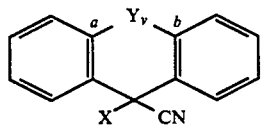

Wherein S, Y and v are as defined for formula I. These compounds are used in the synthesis of compounds having the formula I, and are active muscarinic receptor antagonists.

The present invention further relates to a pharmaceutical composition for treating or preventing a disease associated with the altered motility or tone of smooth muscle in a mammal, including a human, such as irritable bowel syndrome, diverticular disease, urinary incontinence, oesophageal achalasia and chronic obstructive airways disease, comprising a compound of the formula I, or a pharmaceutically acceptable salt thereof, and a pharmaceutically acceptable carrier.

The present invention further relates to a method of treating or preventing a disease associated with the altered motility or tone of smooth muscle in a mammal, including a human, such as irritable bowel syndrome, diverticular disease, urinary incontinence, oesophageal achalasia and chronic obstructive airways disease, comprising administering to a mammal an amount of a compound of the formula I, or a pharmaceutically acceptable salt thereof, effective in preventing or alleviating such disease.

DETAILED DESCRIPTION OF THE INVENTION

The compounds of the formula (I) may be prepared from the compounds of the formulae:

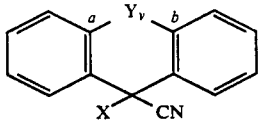

and their pharmaceutically acceptable salts, where X, Y and v are as defined for formula (I). These compounds are not only useful intermediates to the compounds of the formula (I), but are also muscarinic receptor antagonists. These intermediates, excluding the compound "3-benzylmethylamino-1,1-diphenylpropyl cyanide", which is disclosed, purely as a synthetic intermediate, in J. Chem. Soc., 500, (1949), also form a part of the invention.

The pharmaceutically acceptable salts of the compounds of formula (I) include acid addition salts such as the hydrochloride, hydrobromide, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, vol. 66, No. 1, Jan. 1977, pages 1-19. These salts can be prepared conventionally, e.g. by mixing a solution of the free base and the acid in a suitable solvent, e.g. ethanol, and recovering the acid addition salt either as a precipitate, or by evaporation of the solution.

The compounds of the formula (I) can be prepared by a number of routes, including the following:

ROUTE A this route involves the hydrolysis of the nitriles of the formula (II) in a conventional manner, e.g. using concentrated aqueous mineral acid (typically concentrated aqueous $H_2SO_4$), aqueous alkali (e.g. aqueous potassium hydroxide) or alkaline hydrogen peroxide (typically $H_2O_2$/NaOH).

The hydrolysis is preferably carried out using concentrated sulphuric acid, preferably 80-98% sulphuric acid and most preferably 90% $H_2SO_4$, with heating at e.g. 80°-110° C. and most preferably at about 100° C. The product (I) can then be isolated and purified by conventional procedures. Clearly any cyano substituents on $R^4$ are also likely to be hydrolysed to carbamoyl or carboxy, any alkanoyloxy substituents to hydroxy, and any alkoxycarbonyl substituents to carboxy.

The starting materials of the formula (II) can be obtained conventionally as will be known to those skilled in the art, e.g. as follows:

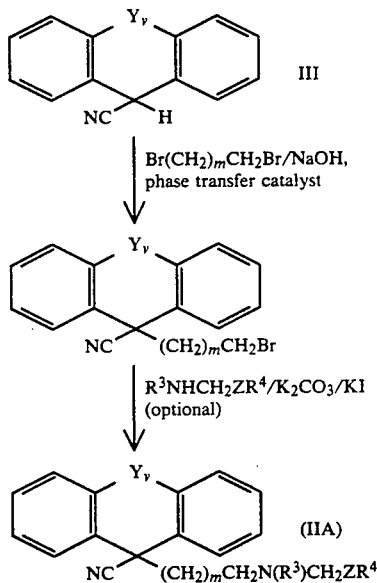

Formula (IIA) above represents compounds of the formula II wherein $R^1$ and $R^2$ are each hydrogen.

The above methodology is illustrated in detail in the Examples.

The starting materials used in the above reaction schemes are either known compounds or can again be prepared by conventional techniques. As stated previously, the preparation of "3-benzylmethylamino-1,1-diphenylpropyl cyanide" is described in Dupre et al. in J. Chem. Soc., 500 (1949), and similar cyanides may be prepared analogously. See also Moffett and Aspergren, J. Amer. Chem. Soc., 4451 (1957); GB 1,129,955, GB 1,147,832, CA 795,330, U.S. Pat. No. 4,335,122 and Cheney et al. in J. Org. Chem., 17, 770 (1952).

An alternative route is as follows:

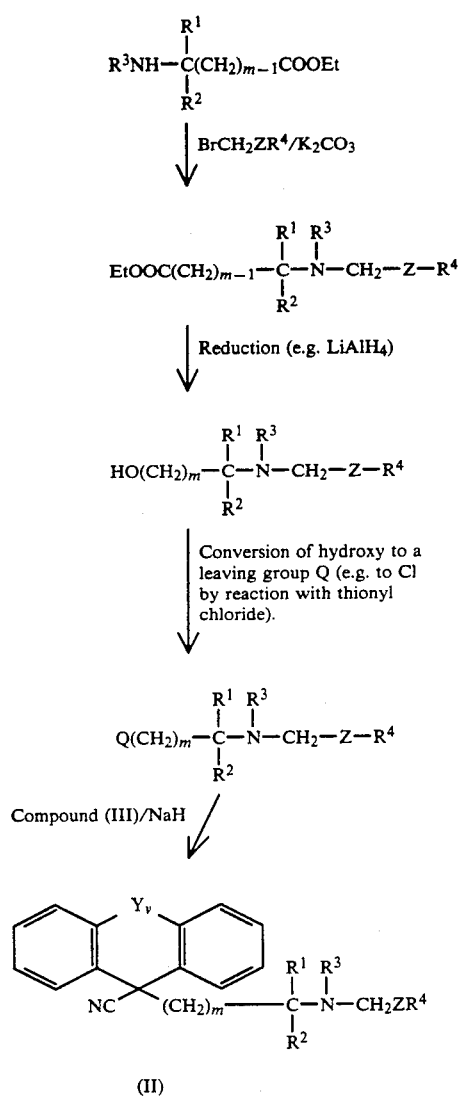

(II)

The methyl ester starting materials are better known compounds (particularly the aminoacid derivatives in which m=1), or can be obtained by conventional techniques, e.g. as follows:

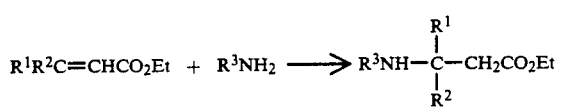

ROUTE B:

This can be illustrated as follows:

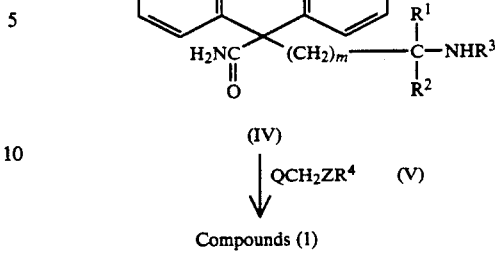

(IV)

↓ QCH$_2$ZR$^4$    (V)

Compounds (I)

$R^1$, $R^2$, $R^3$, $R^4$, m and Z are as defined for formulae (I) and Q is a leaving group, e.g. Br, Cl, I, $C_1$-$C_4$ alkanesulfonyloxy (e.g. methanesulfonyloxy), benzenesulfonyloxy, toluenesulfonyloxy (e.g. p-toluenesulfonyloxy) or trifluoromethanesulfonyloxy. Preferably, Q is Cl, Br, I or methanesulfonyloxy.

The reaction is preferably carried out in the presence of an acid acceptor such as sodium bicarbonate, sodium or potassium carbonate or triethylamine, and in a suitable organic solvent, e.g. acetonitrile or dioxan, at up to the reflux temperature. Reaction temperatures of 60°-110° C. are generally desirable and it is most convenient to carry out the reaction under reflux. Iodo is a particularly suitable leaving group but since the starting materials (V) are sometimes most conveniently available as chlorides, the reaction can also be carried out using the compound (V) as a chloride but in the presence of an iodide such as sodium or potassium iodide.

The starting materials (IV) can be prepared by the debenzylation of the corresponding compounds of the formula (I) and (IB) in which Z is a direct link and $R^4$ is phenyl, these being preparable, of course, by Route A. The debenzylation is typically carried out by catalytic hydrogenation, e.g. using H$_2$/Pd/C in ethanol, or by the use of formic acid in methanol in the presence of Pd/C.

ROUTE C this route can be illustrated as follows:

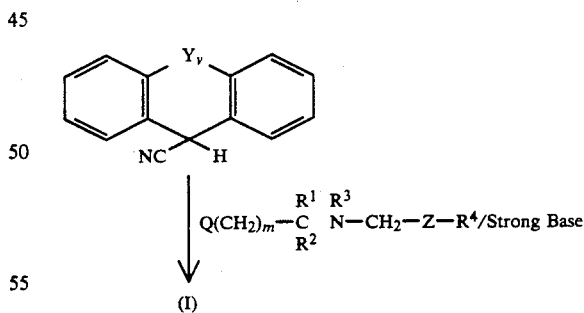

$R^1$, $R^2$, $R^3$, $R^4$, Z, v and m are as defined for formula (I) and Q is a leaving group.

The reaction is carried out conventionally, e.g. in an organic solvent such as toluene at 60°-110° C., preferably under reflux, and in the presence of a storng base such as sodium hydride or sodamide.

Q is preferably Cl, Br or I.

The starting materials can be obtained conventionally (see e.g. Route A). ROUTE D The compounds of the formulae (IA) and (IB) in which Z is CH$_2$ and $R^4$ is 2- or 4-pyridyl or pyrazinyl can also be prepared by reacting a compound of the formula (IVA) or (IVB) (see Route B) with 2- or 4-vinylpyridine or 2-vinylpyrazine. The reaction is typically carried out in a suitable organic solvent, e.g. dioxan, with heating, typically at about 60°–110° C. and preferably under reflux. In some instances, the presence of a basic (preferably a stong base which is soluble in an organic solvent, such as N-benzyltrimethylammonium hydroxide ["Triton B"]) or acidic (preferably a $C_1$–$C_4$ alkanoic acid) catalyst may be beneficial. The product can then be isolated and purified conventionally.

Some of the compounds of the formula (I) in which $R^4$ is a substituted phenyl group can be converted to other compounds of the formula (I) as follows:

(a) A —$CO_2$($C_1$–$C_4$ alkyl) substituent on the phenyl group can be reduced to —$CH_2OH$. Lithium aluminium hydride is the most suitable reducing agent. The reaction is typically carried out in a suitable organic solvent, e.g. ether, at between 0° and room temperature. It is generally most convenient to use the starting material in the form of its methyl ester.

(b) hydroxy substituent on the phenyl group can be converted to —OCO($C_1$–$C_4$ alkyl) by acylation using a $C_1$–$C_4$ alkanoyl chloride or bromide, or an alkanoic anhydride of the formula ($C_1$–$C_4$ alkyl.CO)$_2$O. The presence of an acid acceptor is preferable. The reaction is typically carried out at about room temperature in a suitable organic solvent, e.g. dioxan.

(c) A —CO($C_1$–$C_4$ alkyl) substituent on the phenyl group can be reduced to a substituent of the formula —CH(OH)($C_1$–$C_4$ alkyl). Suitable reducing agents include sodium borohydride and lithium aluminium hydride. The reaction is typically carried out at between 0° and room temperature in a suitable organic solvent, e.g. methanol. Sodium borohydride is the preferred reducing agent.

(d) A —$(CH_2)_p$COO($C_1$–$C_4$ alkyl) substituent, preferably where the alkyl group is methyl, can be converted to —$(CH_2)_p$CONR$^7$R$^8$ by reaction with ammonia or the appropriate amine R$^7$R$^8$NH. When R$^7$ and R$^8$ are both H, the use of aqueous (0.880) ammonia is generally most convenient, although the reaction can be carried out using ammonia in an organic solvent such as methanol or ethanol, or ammonia neat in a bomb. The reaction with methylamine is most conveniently carried out in ethanol. Although in some instances the reaction may proceed at a satisfactory rate at room temperature, heating at up to 120°, preferably 60° to 100° C., is often necessary. For volatile amines, the reaction is best carried out in a bomb.

(e) An amino substituent on the phenyl group can be converted to —NHSO$_2$($C_1$–$C_4$ alkyl) by reaction with a $C_1$–$C_4$ alkanesulphonyl chloride or bromide or $C_1$–$C_4$ alkanesulphonic anhydride. The presence of an acid acceptor such as pyridine, triethylamine, sodium bicarbonate or sodium or potassium carbonate, is preferable. It is often most convenient, particularly when a sulphonyl chloride is used, to carry out the reaction is pyridine, the pyridine functioning as both the solvent and the acid acceptor. Heating is not usually necessary: normally the reaction will proceed at a satisfactory rate at room temperature.

(f) An amino substituent on the phenyl group can also be converted to sulphamoyl by reaction with sulphamide, typically under reflux in an organic solvent such as dioxan.

(g) A hydroxy substituent can be converted to $C_1$–$C_4$ alkoxy firstly by reaction with a base such as potassium carbonate, and then by reaction with a $C_1$–$C_4$ alkyl iodide. The reaction is preferably carried out at the reflux temperature in a solvent such as acetone or dioxan.

(h) An acetyl substituent can be converted to —C(OH)(CH$_3$)$_2$ by reaction with methyllithium, methylmagnesium bromide, methylmagnesium iodide or methylmagnesium chloride. The reaction is typically carried out in a solvent such as ether at a temperature of from 0° C to room temperature.

(i) An iodo substituent can be converted to $C_1$–$C_4$ alkoxycarbonyl by reaction, typically at about room temperature, with carbon monoxide in a $C_1$–$C_4$ alkanol containing a base [e.g. potassium carbonate] and a palladium (II) catalyst [e.g. bis(triphenylphosphine)palladium (II) chloride]. and (j) A cyano substituent on the phenyl group can be reduced to aminomethyl, typically by catalytic hydrogenation, e.g. using H$_2$/Pd/C in ethanol containing a small amount of concentrated hydrochloric acid, or by using formic acid in methanol in the presence of Pd/C.

The selectivity of the compounds as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% O$_2$ and 5% CO$_2$. Contractions of the ileum, bladder and trachea are recorded using a isotonic (ileum) or isometric transducer (bladder and trachea). The frequency of contraction of the spontaneously beating right atrium is derived from isometrically recorded contractions.

Dose-response curves to either acetylcholine (ileum) or carbachol (trachea, bladder and right atrium) are determined using a 1–5 minute contact time for each dose of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiological salt solution containing the second concentration of test compound and the above procedure is repeated. Typically four concentrations of the test compound are evaluated on each tissue.

The concentration of the test compound which causes a doubling of the agonist concentration to produce the original response is determined (pA$_2$ value—Arunlakshana and Schild (1959), Brit. J. Pharmacol., 14, 48–58). Using the above analytical techniques, tissue selectivity for muscarinic receptor antagonists is determined.

Activity against agonist induced bronchoconstriction, gut or bladder contractility in comparison with changes in heart rate is determined in the anaesthetised dog. Oral activity is assessed in the conscious dog determining compound effects on, for example, heart rate, pupil diameter and gut motility.

Compound affinity for other cholinergic sites is assessed in the mouse after either intravenous or intraperitoneal administration. Thus, the dose to cause a doubling of pupil size is determined as well as the dose to inhibit by 50% the salivation and tremor responses to intravenous oxotremorine.

For administration to man in the curative or prophylactic treatment of diseases associated with the altered motility and/or tone of smooth muscle, such as irritable bowel syndrome, diverticular disease, urinary incontinence, oesophageal achalasia and chronic obstructive airways disease, oral dosages of the compounds will generally be in the range of from 3.5 to 350 mg daily for an average adult patient (70 kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to 35 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

The following Examples, in which all temperature are in 0° C., illustrate the invention:

EXAMPLE 1

Preparation of
5-(N-benzyl-N-methylamino)-2,2-diphenylpentanamide

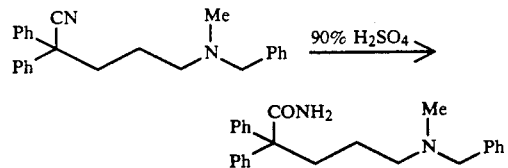

4-(N-Benzyl-N-methylamino)-1-cyano-1,1-diphenylbutane (2%—see Preparation 2) was dissolved in 90% sulphuric acid (11 l) and the solution heated at 100° for 3 hours. The solution was allowed to cool to room temperature then poured slowly into water (100 ml). The mixture was made basic (pH 10) by the addition of 10% aqueous sodium carbonate and extracted with dichloromethane (3×50 ml). The combined dichloromethane extracts were dried (MgSO₄) and concentrated in vacuo to leave the title compound as a colourless foam, yield 1.9 g.

¹H N.M.R. (CDDl₃ δ=7.40–7.20 (m, 15 H); 5.90 (brs, 1R); 5.75 (brs, 1H); 3.45 (s, 2H); 2.45–2.35 (m, 4H); 2.15 (s, 3H); 1.50–1.35 (m, 2H) ppm.

EXAMPLE 2

Preparation ob
2,2-diphenyl-4-(N-benzyl-N-methylamino)butanamide

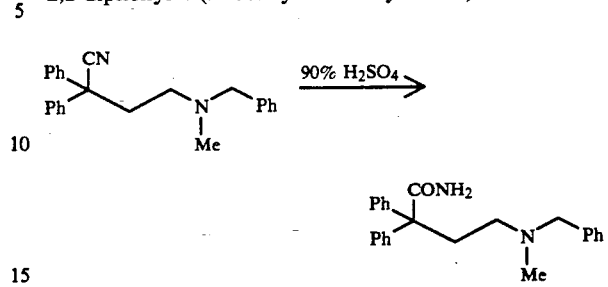

A solution of 3-(N-benzyl-N-methylamino)-1-cyano-1,1-diphenylpropane (11.1 g—see Preparation 5) in 90% sulphuric acid (66 ml) was heated at 100° for 1 hour. The mixture was allowed to cool to room temperature and poured into ice/water (300 ml). The aqueous mixture was basified with saturated aqueous sodium carbonate and extracted with dichloromethane (3×100 ml). The combined dichloromethane extracts were dried (MgSO₄) and concentrated in vacuo to give the title compound, yield 10.6 g. A sample recrystallised from ethanol had a melting point of 145°–148°.

Analysis %: Found: C, 78.64; H, 7.30; N, 7.73; Calculated for $C_{24}R_{26}N_2O \cdot \frac{1}{2}H_2O$: C, 78.43; H, 7.40; N, 7.62.

¹H N.M.R. (CDCl₃) δ=7.40–7.20 (m, 15H); 7.05 (brs, 1H); 5.75 (brs, 1H); 3.45 (s, 2H); 2.65 (m, 2H); 2.40 (m, 2H); 2.20 (s, 3H) ppm.

EXAMPLE 3

Preparation of
5-(N-benzyl-N-methylamino)-2,2-diphenyl-5-methylhexanamide

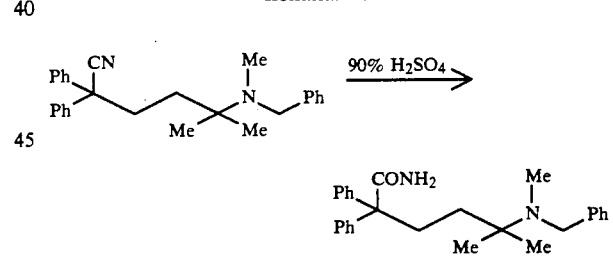

A solution of 4-(N-benzyl-N-methylamino)-1-cyano-1,1-diphenyl-4-methylpentane (1.0 g—see Preparation 12) in 90% sulphuric acid (10 ml) was heated at 90° for 1 hour. The mixture was poured onto ice (100 g), basified to a pH of about 12 by the addition of 40% aqueous sodium hydroxide and extracted with dichloromethane (2×100 ml). The combined dichloromethane extracts were dried (MgSO₄) and concentrated in vacuo to give a gum which was purified by column chromatography on silica eluting with dichloromethane containing methanol (0% up to 4%). The product-containing fractions were combined and concentrated in vacuo to give the title compound as a gum, yield 0.6 g.

¹H N.M.R. (CDCl₃) δ=7.45–7.20 (m, 15H); 5.65 (brs, 1H); 5.45 (brs, 1H); 3.45 (s, 2H); 2.70–2.60 (m, 2H); 2.00 (s, 3H); 1.50–1.40 (m, 2H); 1.10 (s, 6H) ppm.

EXAMPLE 4

Preparation of 2,2-diphenyl-5-[N-(3,4-methylenedioxybenzyl)-N-methylamino]pentanamide

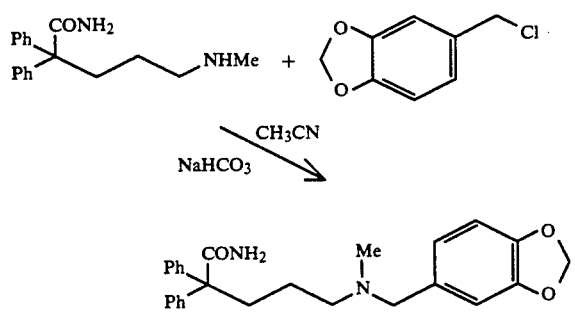

A mixture containing 2,2-diphenyl-5-methylaminopentanamide (0.29 g—see Preparation 3), 3,4-methylenedioxybenzyl chloride (0.18 g—commercially available), sodium bicarbonate (0.1 g) and acetonitrile (20 ml) was heated under reflux for 3 hours. The mixture was partitioned between dichloromethane and 10% aqueous sodium carbonate, the layers separated and the dichloromethane layer dried (MgSO4). The solution was concentrated in vacuo and the residue purified by column chromatography on silica, eluting with dichloromethane containing methanol (0% up to 6%). The product-containing fractions were combined and concentrated in vacuo to give the title compound as an oil, yield 0.22 g.

Analysis %: Found: C, 72.61; H, 6.62; N, 6.49; Calculated for $C_{26}H_{28}N_2O_3 1/5 CH_2Cl_2$: C, 72.63; H, 6.61; N, 6.47.

$^1$H N.M.R. (CDCl$_3$) δ=7.50-7.25 (m, 10H); 6.85-6.70 (m, 3H); 6.00 (s, 2H); 5.85 (brs, 1H); 5.55 (brs, 1H); 3.40 (s, 2H); 2.50-2.30 (m, 4H); 2.15 (s, 3H); 1.50-1.35 (m, 2H) ppm.

EXAMPLE 5

Preparation of 2,2-diphenyl-5-[N-(3,4-methylenedioxyphenethyl)-N-methylamino]pentanamide

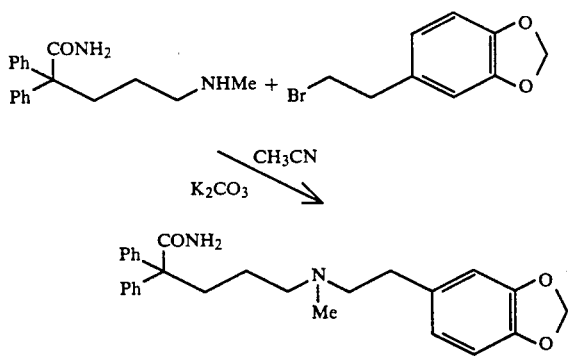

A mixture containing 2,2-diphenyl-5-methylaminopentanamide (1.0 g—see Preparation 3), 3,4-methylenedioxyphenethyl bromide (0.9 g), anhydrous potassium carbonate (2.0 g) and acetonitrile (20 ml) was heated under reflux for 8 hours. The mixture was partitioned between dichloromethane (30 ml) and 5% sodium carbonate (20 ml), the layers separated and the aqueous layer extracted with dichloromethane (3×20 ml). The combined dichloromethane extracts were dried (MgSO4) and concentrated in vacuo to give an oil which was purified by column chromatography on silica eluting with dichloromethane containing methanol (0% up to 5%). The product-containing fractions were combined and concentrated in vacuo to give the title compound as a foam, yield 0.58 g, m.p. 89°-90°.

Analysis %:

Found: C, 75.80; H, 7.21; N, 6.41;

Calculated for $C_{27}H_{30}N_2O_3$: C 75.32; H, 7.02; N, 6.51;

$^1$H N.M.R. (CDCl$_3$) δ=7.45-7.25 (m, 10H); 6.80-6.60 (m, 3H); 5.90 (s, 2H); 5.85 (brs, 1H); 5.45 (brs, 1H); 2.70 (m, 2H); 2.55 (m, 2H); 2.40 (m, 4H); 2.25 (s, 3H); 1.45-1.30 (m, 2H) ppm.

EXAMPLE 6

Preparation of 2,2-diphenyl-5-[N-(4-methoxyphenethyl)-N-methylamino]pentanamide

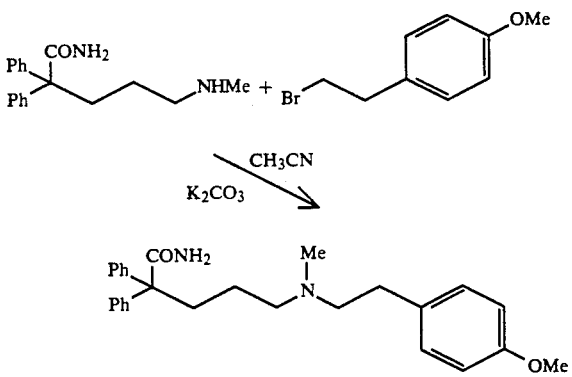

A mixture containing 2,2-diphenyl-5-methylaminopentanamide (0.29 g—see Preparation 2), 4-methoxyphenethyl bromide (0.22 g), anhydrous potassium carbonate (0.5 g) and acetonitrile (30 ml) was heated under reflux for 3 hours. The mixture was partitioned between dichloromethane (50 ml) and 5% aqueous sodium carbonate (50 ml), the layers separated and the aqueous layer extracted with dichloromethane (3×50 ml). The combined dichloromethane extracts were dried (MgSO4) and concentrated in vacuo to give an oil which was purified by column chromatography on silica eluting with dichloromethane containing methanol (0% up to 5%). The product-containing fractions were combined and concentrated in vacuo to give the title compound as a foam, yield 0.22 g.

Analysis %: Found C, 76.52; H, 7.63; N, 6.53; Calculated for $C_{27}H_{32}N_2O_2.\frac{1}{2}H_2O$: C, 76.20; H, 7.81; N, 6.58.

$^1$H N.M.R. (CDCl$_3$) δ=7.40-7.30 (m, 10H); 7.10 (d, 2H); 6.85 (d, 2H); 5.85 (brs, 1H); 5.60 (brs, 1H); 3.80 (s, 3H); 2.80-2.70 (m, 2H); 2.65-2.55 (m, 2H); 2.50-2.35 (m, 4H); 2.25 (s, 3H); 1.45-1.35 (m, 2H) ppm.

EXAMPLE 7

Preparation of 2,2-diphenyl-5-[N-(4-hydroxymethylphenethyl)-N-methylamino]pentanamide

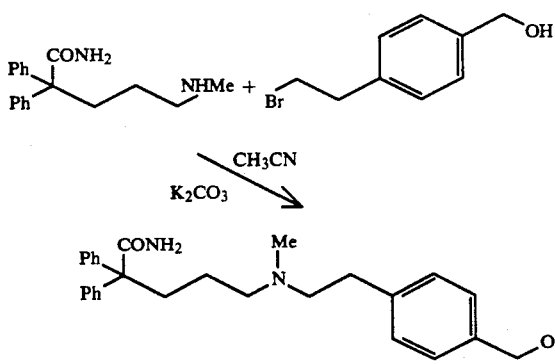

A mixture containing 2,2-diphenyl-5-methylaminopentanamide (0.24 g—see Preparation 3), 4-hydroxymethylphenethyl bromide (0.19 g), anhydrous potassium carbonate (0.5 g) and acetonitrile (20 ml) was heated under reflux for 4 hours. The mixture was partitioned between dichloromethane (50 ml) and 5% aqueous sodium carbonate (30 ml), the layers separated and the aqueous layer extracted with dichloromethane (3×30 ml). The combined dichloromethane extracts were dried (MgSO4) and concentrated in vacuo to give a gum which was purified by column chromatography on silica eluting with dichloromethane containing methanol (0% up to 5%). The product-containing fractions were combined and concentrated in vacuo to give the title compound as a foam, yield 0.14 g.

Analysis %: Found: C, 76.25; H, 7.67; N, 6.58; Calculated for $C_{27}H_{32}N_2O_2.\frac{1}{2}H_2O$: C, 76.20; H, 7.81; N, 6.58.

$^1$H N.M.R. (CDCl$_3$) δ=7.40–7.10 (m, 14H); 5.95–5.80 (m, 3H); 4.60 (s, 2H); 2.80–2.70 (m, 2H); 2.60–2.50 (m, 2H); 2.45–2.30 (m, 4H); 2.25 (s, 3H); 1.40–1.30 (m, 2H) ppm.

EXAMPLE 8

Preparation of 2,2-diphenyl-5-[N-{2-(1,4-benzodioxan-6-yl)ethyl}-N-methylamino]pentanamide

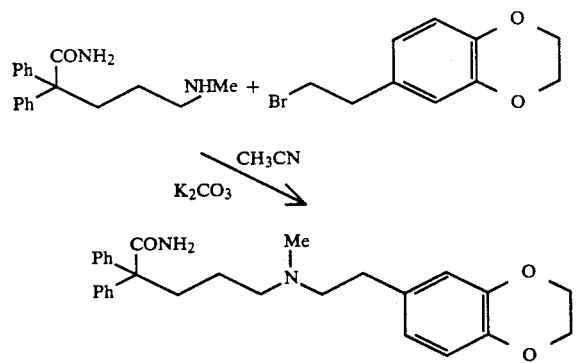

A mixture containing 2,2-diphenyl-5-methylaminopentanamide (0.36 g—see Preparation 1), 6-(2-bromoethyl)-1,4-benzodioxan (0.32 g), anhydrous potassium carbonate (0.75 g) and acetonitrile (20 ml) was heated under reflux for 16 hours. The mixture was partitioned between dichloromethane (50 ml) and 10% aqueous sodium carbonate (30 ml), the layers separated and the aqueous layer extracted with dichloromethane (3×20 ml). The combined dichloromethane extracts were dried (MgSO4) and concentrated in vacuo to give an oil which was purified by column chromatography on silica eluting with dichloromethane containing methanol (0% up to 5%). The product-containing fractions were combined and concentrated in vacuo to give a foam which was further purified by column chromatography on alumina eluting with dichloromethane containing methanol (0% up to 5%). The product-containing fractions were combined and concentrated in vacuo to give the title compound as a foam, yield 0.11 g.

Analysis %: Found: C, 74.40; H, 7.16; H, 6.20; Calculated for $C_{28}H_{32}N_2O_3.1/10\ CH_2Cl_2$: C, 74.31; H, 7.13; N, 6.19.

$^1$H N.M.R. (CDCl$_3$) δ=7.45–7.25 (m, 10H); 6.80–6.65 (m, 3H); 5.90 (brs, 1H); 5.50 (brs, 1H); 4.20 (s, 4H); 2.70–2.50 (m, 4H); 2.45–2.35 (m, 4H); 2.25 (s, 3H); 1.40–1.30 (m, 2H) ppm.

EXAMPLE 9

Preparation of 2,2-diphenyl-5-[N-(4-hydroxyphenethyl)-N-methylamino]pentanamide

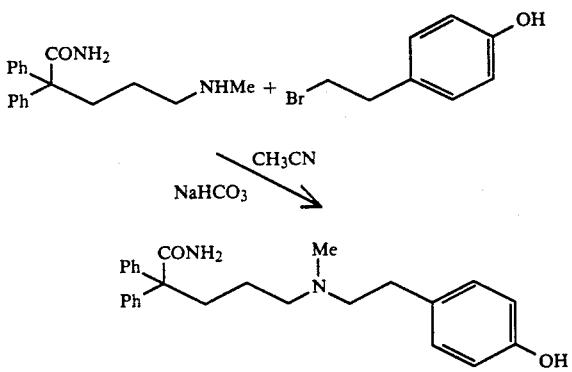

A mixture containing 2,2-diphenyl-5-methylaminopentanamide (0.36 g—see Preparation 3), 4-hydroxyphenethyl bromide (0.26 g), sodium bicarbonate (0.5 g) and acetonitrile (20 ml) was heated under reflux for 16 hours. The mixture was partitioned between dichloromethane (40 ml) and aqueous sodium bicarbonate (30 ml), the layers separated and the aqueous layer extracted with dichloromethane (2×30 ml). The combined dichloromethane extracts were concentrated in vacuo to give an oil which was purified by column chromatography on silica eluting with dichloromethane containing methanol (0% up to 10%). The product-containing fractions were combined and concentrated in vacuo to give a foam which was further purified by column chromatography on alumina eluting with dichloromethane containing methanol (0% up to 10%). The product-containing fractions were combined and concentrated in vacuo to give the title compound as a foam, yield 0.09 g.

Analysis %: Found: C, 75.34; H, 7.44; N, 6.57; Calculated for $C_{26}H_{30}N_2O_2.1/10\ CH_2Cl_2$: C, 75.97; H, 7.36; N, 6.81;

$^1$H N.M.R. (CDCl$_3$) δ=7.40–7.20 (m, 11H); 7.00 (d, 2H); 6.70 (d, 2H); 5.85 (brs, 1H); 5.65 (brs, 1H); 2.75–2.65 (m, 2H); 2.60–2.50 (m, 2H); 2.45–2.35 (m, 4H); 2.25 (s, 3H); 1.45–1.30 (m, 2H) ppm.

EXAMPLE 10

Preparation of 2,2-diphenyl-5-(N-methyl-N-phenethylamino)pentanamide

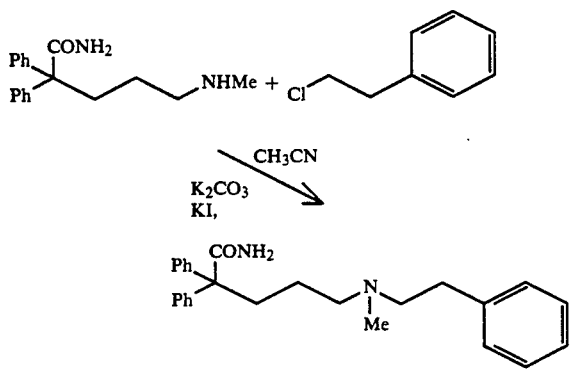

A mixture containing 2,2-diphenyl-5-methylaminopentanamide (0.28 g—see Preparation 3), phenethyl chloride (0.14 g) anhydrous potassium carbonate (0.58 g), anhydrous potassium iodide (0.3 g) and acetonitrile (10 ml) was heated under reflux for 16 hours. The mixture was partitioned between dichloromethane (30 ml) and 10% aqueous sodium carbonate (30 ml), the layers separated and the aqueous layer extracted with dichloromethane (2×20 ml).

The combined dichloromethane extracts were dried (MgSO$_4$) and concentrated in vacuo to give an oil which was purified by column chromatography on silica eluting with dichloromethane containing methanol (0% up to 5%). The product-containing fractions were combined and concentrated in vacuo to give the title compound as a foam, yield 0.14 g.

Analysis %: Found: C, 78.83; H, 7.74; N, 7.05; Calculated for $C_{26}H_{30}N_2O.1/10\ CH_2Cl_2$: C, 79.05; H, 7.65; N, 7.09.

$^1$H N.M.R. (CDCl$_3$) δ=7.45–7.15 (m, 15H); 5.85 (brs, 1H); 5.45 (brs, 1H); 2.80 (m, 2H); 2.60 (m, 2H); 2.40 (m, 4H); 2.25 (s, 3H); 1.45–1.35 (m, 2H) ppm.

EXAMPLE 11

Preparation of 2,2-diphenyl-5-[N-(4-chlorophenethyl)-N-methylamino]pentanamide

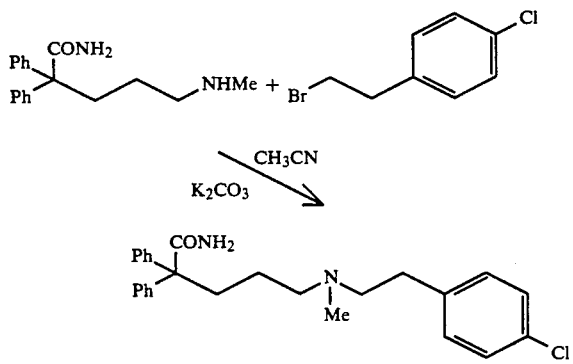

A mixture containing 2,2-diphenyl-5methylaminopentanamide (0.3 g—see Preparation 3), 4-chlorophenethyl bromide (0.234 g—see Preparation 7), anhydrous potassium carbonate (0.4 g) and acetonitrile (10 ml) was heated under reflux for 5 hours. The mixture was concentrated in vacuo and the residue partitioned between dichloromethane (30 ml) and 10% aqueous potassium carbonate (30 ml). The layers were separated and the aqueous layer extracted with dichloromethane (3×20 ml). The combined dichloromethane extracts were dried (MgSO$_4$) and concentrated in vacuo to give a gum which was purified by column chromatography on silica eluting with dichloromethane containing methanol (5% up to 10%). The product-containing fractions were combined and concentrated in vacuo to give the title compound as a gum, yield 0.306 g.

Analysis %: Found: C, 72.58; H, 6.90; N, 6.40; Calculated for $C_{26}H_{29}ClN_2O.1/6\ CH_2Cl_2$: C, 72.36; H, 6.81; N, 6.45.

$^1$H N.M.R. (CDCl$_3$) δ=7.40–7.20 (m, 12H); 7.10 (d, 2H); 5.70 (brs, 1H); 5.50 (brs, 1H); 2.75–2.70 (m, 2H); 2.60–2.50 (m, 2H); 2.45–2.35 (m, 4H); 2.25 (s, 3H); 1.45–1.30 (m, 2H) ppm.

EXAMPLE 12

Preparation of 2,2-diphenyl-5-[N-methyl-N-(4-methylphenethyl)amino]pentanamide

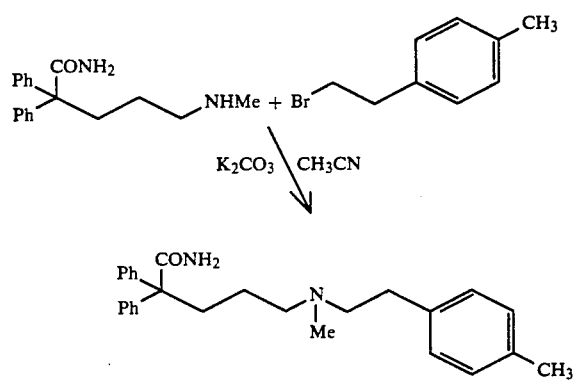

A mixture containing 2,2-diphenyl-5-methylaminopentanamide (0.28 g—see Preparation 3), 4-methylphenethyl bromide (0.2 g), anhydrous potassium carbonate (0.28 g) and acetonitrile (10 ml) was heated under reflux for 16 hours. The mixture was partitioned between dichloromethane (30 ml) and 10% aqueous sodium carbonate (30 ml), the layers separated and the aqueous layer extracted with dichloromethane (3×20 ml). The combined dichloromethane extracts were dried (MgSO$_4$) and concentrated in vacuo to give a gum which was purified by column chromatography on silica eluting with dichloromethane containing methanol (0% up to 6%). The product-containing fractions were combined and concentrated in vacuo to give the title compound as a foam, yield 0.19 g.

Analysis %: Found: C, 80.64; H, 8.24; N, 7.06; Calculated for $C_{27}H_{32}N_2O$: C, 80.95; H, 8.05; N, 6.99.

$^1$H N.M.R. (CDCl$_3$) δ=7.40–7.05 (m, 14H); 5.80 (brs, 1H); 5.40 (brs, 1H); 2.80 (m, 2H); 2.65 (m, 2H); 2.50–2.40 (m, 4H); 2.35 (s, 3H); 2.30 (s, 3H) 1.45 (m, 2H) ppm.

EXAMPLE 13

Preparation of
2,2-diphenyl-5-[N-(4-cyanophenethyl)-N-methyl-amino]pentanamide

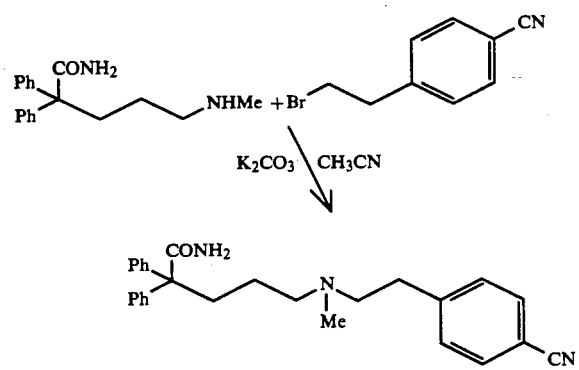

A mixture containing 2,2-diphenyl-5-methylaminopentanamide (1.0 g—see Preparation 3), 4-cyanophenethyl bromide (0.82 g), anhydrous potassium carbonate (2.0 g) and acetonitrile (30 ml) was heated under reflux for 10 hours. The mixture was partitioned between dichloromethane (50 ml) and 10% aqueous sodium carbonate (30 ml), the layers separated and the aqueous layer extracted with dichloromethane (2×30 ml). The combined dichloromethane extracts were dried (MgSO$_2$) and concentrated in vacuo to give an oil which was purified by column chromatography on silica eluting with dichloromethane containing methanol (0% up to 6%). The product-containing fractions were combined and concentrated in vacuo to give an oil which was further purified by column chromatography on silica eluting with dichloromethane containing methanol (0% up to 4%). The product-containing fractions were combined and concentrated in vacuo to give the title compound as an oil, yield 0.22 g.

Analysis % Found: C,77.38; H,7.10; N,10.01; Calculated for C$_{27}$H$_{29}$N$_3$O.1/10 CH$_2$Cl$_2$: C,77.20H,6.96; N,10.00.

$^1$H N.M.R. (CDCl$_3$) δ=7.60 (d, 2H); 7.40–7.20 (m,12H); 5.60 (brs, 1H); 5.40 (brs 1H); 2.80 (m,2H); 2.60 (m, 2H); 2.40 (m, 4H); 2.20 (m, 3H); 1.40 (m, 2H) ppm.

EXAMPLE 14

Preparation of
2,2-diphenyl-5-[N-{2-(indan-5-yl)ethyl}-N-methylamino]pentanamide

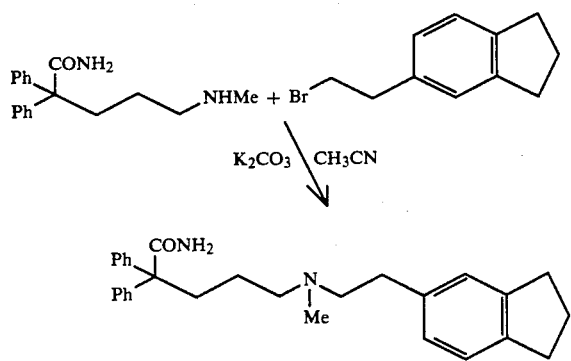

A mixture containing 2,2-diphenyl-5-methylaminopentanamide (0.3 g—see Preparation 3), 5-(2-bromoethyl)indane (0.24 g—see Preparation 6), anhydrous potassium carbonate (0.5 g) and acetonitrile (10 ml) was heated under reflux for 16 hours. The mixture was partitioned between dichloromethane (30 ml) and 10% aqueous sodium carbonate (30 ml), the layers separated and the aqueous layer extracted with dichloromethane (2×20 ml). The combined dichloromethane extracts were dried (MgSO$_4$) and concentrated in vacuo to give an oil which was purified by column chromotography on silica eluting with dichloromethane containing methanol (0% up to 6%). The product-containing fractions were combined and concentrated in vacuo to give the title compound as a foam, yield 0.23 g.

Analysis % Found: C,79.27; H,7.96; N,5.97; Calculated for C$_{29}$H$_{34}$N$_2$O.1/7 CH$_2$Cl$_2$: C,79.38; H,7.81; N,6.38;

$^1$H N.M.R. (CDCl$_3$) δ7.40–7.25 (m, 10H); 7.20–7.15 (d, 1H); 7.10 (s, 1H); 7.00–6.95 (d, 1H); 5.90–5.80 (brs, 1H); 5.45–5.35 (brs, 1H); 2.95–2.85 (m, 4H); 2.80–2.70 (m, 2H); 2.65–2.55 (m, 2H); 2.50–2.40 (m, 4H); 2.30 (s, 3H); 2.15–2.05 (m, 2H); 1.50–1.35 (m, 2H) ppm.

EXAMPLE 15

Preparation of
2,2-diphenyl-5-[N-4-carboxamidophenethyl)-N-methylamino]pentanamide

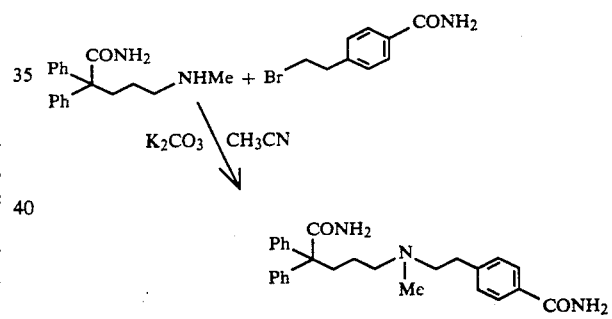

A mixture containing 2,2-diphenyl-5-methylaminopentanamide (0.3 g—see Preparation 3), 4-carboxamidophenethyl bromide (0.24 g), sodium bicarbonate (0.5 g) and acetonitrile (10 ml) was heated under reflux for 5 hours. The mixture was partitioned between dichloromethane (30 ml) and aqueous sodium carbonate (30 ml), the layers separated and the aqueous layer extracted with dichloromethane (2×20 ml). The combined dichloromethane extracts were dried (MgSO$_4$) and concentrated in vacuo to give a gum which was purified by column chromatography on silica eluting with dichloromethane containing methanol (0% up to 6%). The product-containing fractions were combined and concentrated in vacuo to give the title compound as a foam, yield 0.13 g.

Analysis % Found: C,73.09; H, 7.20; N,9.36; Calculated for C$_{27}$H$_{31}$N$_3$O$_2$.1/6 CH$_2$Cl$_2$: C,73.08; H,7.04; N,9.47 $^1$H N.M.R. (CDCl$_3$) δ=7.80–7.70 (d, 2H); 7.40–7.20 (m, 12 H); 6.30–6.05 (brd, 2H); 6.05 (brs, 1H); 5.75 (brs, 1H); 2.80 (m, 2H); 2.60 (m, 2H); 2.40–2.30 (m, 4H); 2.25 (s, 3H); 1.40–1.30 (m, 2H) ppm.

EXAMPLE 16

Preparation of
2,2-diphenyl-5-[N-(4-sulphonamidophenethyl)-N-methylamino]pentanamide

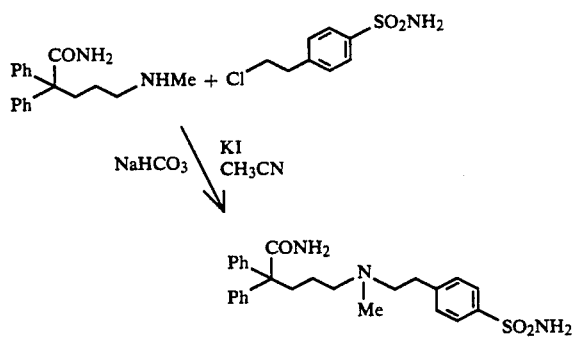

A mixture containing 2,2-diphenyl-5-methylaminopentanamide (0.3 g—see Preparation 3), 4-sulphonamidophenethyl chloride (0.24 g), sodium bicarbonate (0.5 g), anhydrous potassium iodide (0.3 g) and acetonitrile (10 ml) was heated under reflux for 8 hours. The mixture was partitioned between dichloromethane (30 ml) and 10% aqueous sodium carbonate (30 ml), the layers separated and the aqueous layer extracted with dichloromethane (2×20 ml). The combined dichloromethane extracts were dried (MgSO$_4$) and concentrated in vacuo to give a gum which was purified by column chromatography on silica eluting dichloromethane containing methanol (0% up to 8%). The product-containing fractions were combined and concentrated in vacuo to give the title compound as a foam, yield 0.05 g.

Analysis % Found: C,65.77; H,6.81; N,8.88; Calculated for $C_{26}H_{31}N_3O_3S.1/6\ CH_2Cl_2$: C,65.53; H,6.59; N,8.76.

$^1$H N.M.R. (CDCl$_3$) δ=7.85 (d, 2H); 7.45-7.20 (m, 12H); 5.90 (brs, 1H); 5.65 (brs, 1H); 5.10-4.70 (brs, 2H); 2.90-2.80 (m, 2H); 2.70-2.65 (m, 2H); 2.35-2.30 (m, 2H); 2.25-2.15 (m, 2H); 2.20 (s, 3H); 1.25-1.15 (m, 2H) ppm.

EXAMPLE 17

Preparation of
2,2-diphenyl-5-[N-(4-methanesulphonamidophenethyl)-N-methylamino]pentanamide

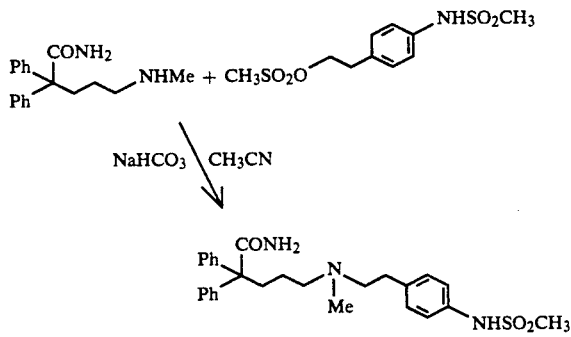

A mixture of 2,2-diphenyl-5-methylaminopentanamide (0.3 g—see Preparation 3), N-[4-(2-methanesulphonyloxyethyl)phenyl]-methanesulphonamide (0.3 g—see Preparation 18), sodium bicarbonate (0.5 g) and acetonitrile (10 ml) was heated under reflux for 8 hours. The mixture was partitioned between dichloromethane (30 ml) and 10% aqueous sodium carbonate (30 ml), the layers separated and the aqueous layer extracted with dichloromethane (2×20 ml). The combined dichloromethane extracts were dried (MgSO$_4$) and concentrated in vacuo to give an oil which was purified by column chromatography on silica eluting with dichloromethane containing methanol (0% up to 6%). The product-containing fractions were combined and concentrated in vacuo to give the title compound as a foam, yield 0.12 g.

Analysis %: Found: C,66.11; H,6.92; N,8.35; Calculated for $C_{27}H_{33}N_3O_3S.\frac{1}{2}H_2O$: C,66.36; H, 7.01; N,8.60.

$^1$H N.M.R. (CDCl$_3$) δ=7.40-7.25 (m, 11H); 7.15 (s, 4H); 5.90 (brs, 1H); 5.70 (brs, 1H) 2.85 (s, 3H); 2.80-2.70 (m, 2H); 2.65-2.55 (m, 2H); 2.45-2.30 (m, 4H); 2.25 (s, 3H); 1.40-1.30 (m, 2H) ppm.

EXAMPLE 18

Preparation of
2,2-diphenyl-5-[N-(3-methylphenethyl)-N-methylamino]pentanamide

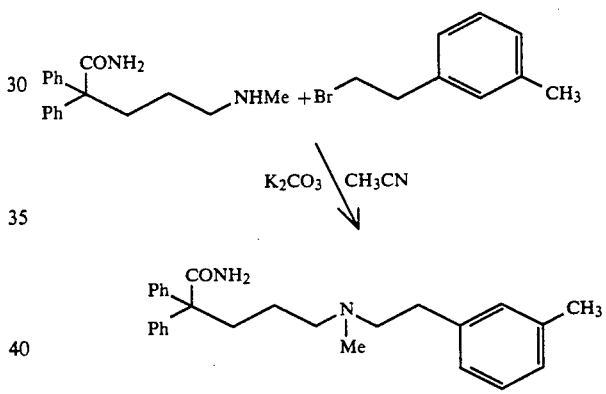

A mixture containing 2,2-diphenyl-5-methylaminopentanamide (0.3 g—see Preparation 3), 3-methylphenethyl bromide (0.21 g), anhydrous potassium carbonate (0.5 g) and acetonitrile (20 ml) was heated under reflux for 8 hours. The mixture was partitioned between dichloromethane (30 ml) and 10% aqueous sodium carbonate (30 ml), the layers separated and the aqueous layer extracted with dichloromethane (2×20 ml). The combined dichloromethane extracts were dried (MgSO$_4$) and concentrated in vacuo to give an oil which was purified by column chromatography on silica eluting with dichloromethane containing methanol (5%). The product-containing fractions were combined and concentrated in vacuo to give the title compound as an oil, yield 0.23 g.

Analysis %: Found: C,77.61; H,7.93; N,6.63; Calculated for $C_{27}H_{32}N_2 1.05\ CH_2Cl_2$: C,77.66; H,7.73; N,6.71.

$^1$H N.M.R. (CDCl$_3$) δ=7.45-7.25 (m, 10H); 7.20 (m, 1H); 7.00 (m, 3H); 5.85 (brs, 1H); 5.40 (brs, 1H) 2.80 (m, 2H); 2.70-2.60 (m, 2H); 2.50-2.40 (m, 4H); 2.35 (s, 3H); 2.30 (s, 3H); 1.50-1.40 (m, 2H) ppm.

EXAMPLE 9

Preparation of
2,2-diphenyl-5-[N-{2-(2,3-dihydrobenzofur-5-yl)ethyl}-N-methylamino]pentanamide

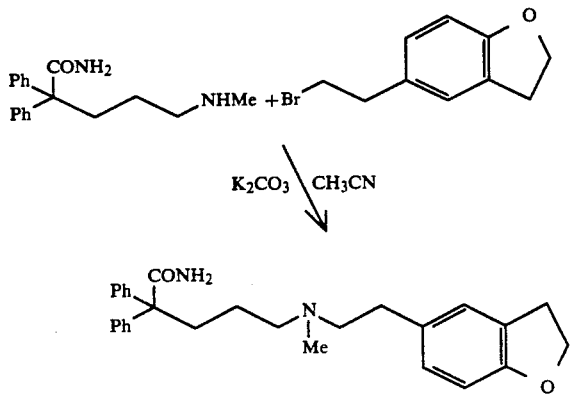

A mixture containing 2,2-diphenyl-5-methylaminopentanamide (0.3—see Preparation 3), 5-(2-bromoethyl)-2,3-dihydrobenzofuran (0.242 g—see Preparation 20), anhydrous potassium carbonate (0.4 g) and acetonitrile (10 ml) was heated under reflux for 5 hours. The mixture was concentrated in vacuo and the residue partitioned between dichloromethane (30 ml) and 10% aqueous potassium carbonate (30 ml). The layers were separated and the aqueous layer extracted with dichloromethane (3×20 ml). The combined dichloromethane extracts were dried (MgSO₄) and concentrated in vacuo to give a gum which was purified by column chromatography on silica eluting with dichloromethane containing methanol (5% up to 10%). The product-containing fractions were combined and concentrated in vacuo to give the title compound as a gum, yield 0.26 g.

Analysis %: Found: C,72.58; H,7.21; N,6.00; Calculated for $C_{28}H_{32}N_2O_2 \cdot \frac{1}{2}CH_2Cl_2$: C,72.67; H, 7.06; N, 5.95.

¹H N.M.R. (CDCl₃) δ=7.40–7.25 (m, 10H); 7.05 (s, 1H); 6.90 (m, 1H); 6.70 (m, 1H); 5.80 (brs, 1H); 5.50 (brs, 1H) 4.55 (t, 2H); 3.15 (t, 2H); 2.80–2.70 (m, 2H); 2.70–2.60 (m, 2H); 2.60–2.50 (m, 2H); 2.50–2.40 (m, 2H); 2.35 (s, 3H); 1.50–1.40 (m, 2H) ppm.

EXAMPLE 20

Preparation of
2,2-diphenyl-5-[N-(4-fluorophenethyl)-N-methylamino]pentanamide

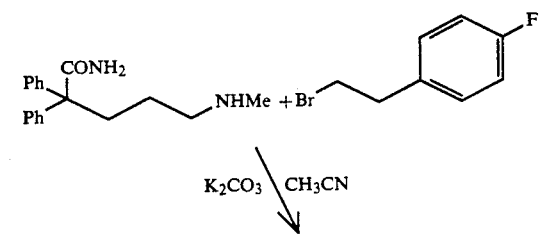

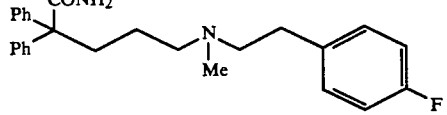

A mixture containing 2,2-diphenyl-5-methylaminopentanamide (0.3 g—see Preparation 3), 4-fluorophenethyl bromide (0.22 g), anhydrous potassium carbonate (0.4 g) and acetonitrile (10 ml) was heated under reflux for 5 hours. The mixture was concentrated in vacuo and the residue partitioned between dichloromethane (20 ml) and 10% aqueous potassium carbonate (20 ml). The layers were separated and the aqueous layer extracted with dichloromethane (3×20 ml). The combined dichloromethane extracts were dried (MgSO₄) and concentrated in vacuo to give a gum which was purified by column chromatography on silica eluting with dichloromethane containing methanol (5% up to 10%). The product-containing fractions were combined and concentrated in vacuo to give the title compound as an oil, yield 0.259 g.

Analysis %: Found C,75.33; H,7.18; N,6.70; Calculated for $C_{26}H_{29}FN_2O \cdot 1/7\ CH_2Cl_2$: C,75.36; H,7.09; N,6.72.

¹H N.M.R. (CDCl₃) δ=7.40–7.25 (m, 10H); 7.20–7.10 (m, 2H); 7.00–6.90 (m, 2H); 5.75 (brs, 1H); 5.45 (brs, 1H); 2.80–2.70 (m, 2H); 2.65–2.55 (m, 2H); 2.50–2.35 (m, 4H); 2.25 (s, 3H); 1.45–1.35 (m, 2H) ppm.

EXAMPLE 21

Preparation of
2,2-diphenyl-5-[N-(3,4-methylenedioxyphenethyl)-N-methylamino]-5-methylhexanamide

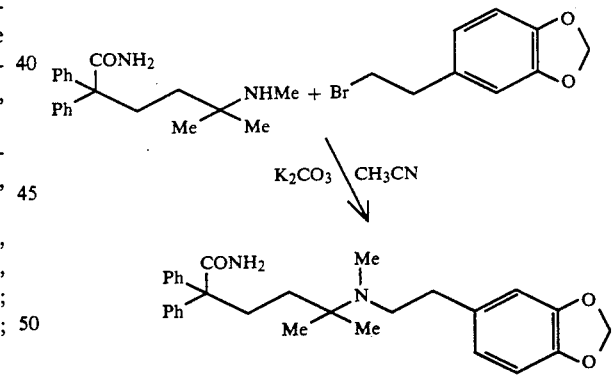

A mixture containing 2,2-diphenyl-5-methyl-5-methylaminohexanamide (0.5 g— see Preparation 13), 3,4-methylenedioxyphenethyl bromide (0.38 g), anhydrous potassium carbonate (0.8 g) and acetonitrile (10 ml) was heated under reflux for 5.5 hours. The mixture was partitioned between dichloromethane (30 ml) and 10% aqueous sodium carbonate (30 ml), the layers separated and the aqueous layer extracted with dichloromethane (3×20 ml). The combined dichloromethane extracts were dried (MgSO₄) and concentrated in vacuo to give an oil which has purified by column chromatography on silica eluting with dichloromethane containing methanol (0% up to 6%). The product-containing fractions were combined and concentrated in vacuo to give an oil which solidified on standing. The solid was recrystallised from ethanol to give the title compound as colourless needles, yield 0.09 g, m.p. 165° (softens at 45°).

Analysis %: Found: C,76.35; H,7.65; N,6.02; Calculated for C29H34N2O3: C,75.95; H,7.47; N,6.11.

¹H N.M.R. (CDCl3) δ=7.45–7.20 (m, 10H); 6.80–6.60 (m, 3H); 5.90 (s, 2H); 5.50 (brs, 2H); 2.70–2.60 (m, 2H); 2.50–2.35 (m, 4H); 2.20 (s, 3H); 1.35–1.25 (m, 2H); 0.95 (s, 6H) ppm.

EXAMPLE 22

Preparation of 2,2-diphenyl-5-[N-(4-fluorophenethyl)-N-methylamino]-5-methylhexanamide

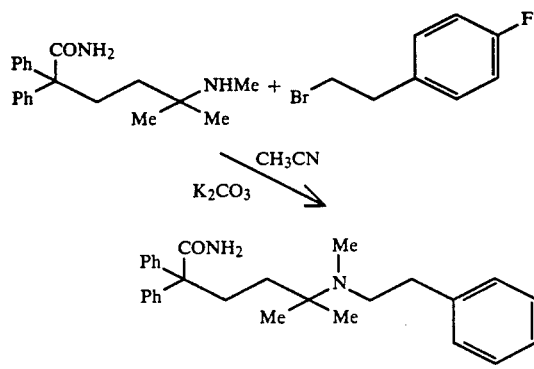

A mixture containing 2,2-diphenyl-5-methyl-5-methylaminohexanamide (0.31 g—see Preparation 13), 4-fluorophenethyl bromide (0.2 g), anhydrous potassium carbonate (0.5 g) and acetonitrile (15 ml) was heated under reflux for 5 hours. The mixture was partitioned between dichloromethane (30 ml) and 10% aqueous potassium carbonate (20 ml), the layers separated and the aqueous layer extracted with dichloromethane (3×20 ml). The combined dichloromethane extracts were dried (MgSO4) and concentrated in vacuo to give an oil which was purified by column chromatography on silica eluting with dichloromethane containing methanol (0% up to 6%). The product-containing fractions were combined and concentrated in vacuo to give the title compound as a foam, yield 0.1 g.

Analysis %: Found: C,74.52; H,7.52; N,6.14; Calculated for C28H33FN2O.H2O: C,74.63; H,7.82; N,6.22.

¹H N.M.R. (CDCl3/CF3CO2D) δ=8.00 (brs, 2H); 7.50–7.00 (m, 14H); 3.60–3.45 (m, 2H); 3.15–3.00 (m, 2H); 2.85 (s, 3H); 2.60–2.45 (m, 2H); 1.75–1.60 (m, 2H); 1.40 (s, 6H) ppm.

EXAMPLE 23

Preparation of 2,2-diphenyl-5-[N-methyl-N-(4-methoxycarbonylmethylphenethyl)amino]pentanamide

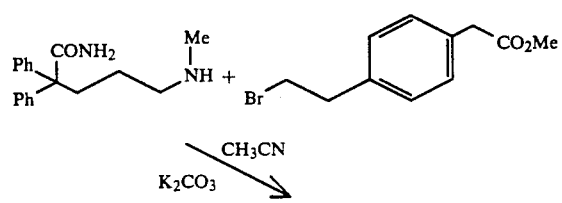

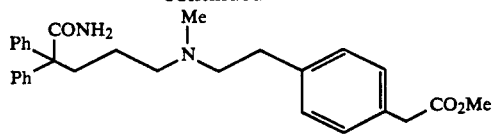

A mixture containing 2,2-diphenyl-5-methylaminopentanamide (0.56 g—see Preparation 3), methyl 4-(2-brom0ethyl)phenylacetate (0.51 g—see Preparation 22), anhydrous potassium carbonate (0.6 g) and acetonitrile (20 ml) was heated under reflux for 5.5 hours. The mixture was partitioned between dichloromethane (70 ml) and 10% aqueous potassium carbonate (50 ml), the layers separated, and the aqueous layer extracted with dichloromethane (2×50 ml). The combined dichloromethane extracts were dried (MgSO4) and concentrated in vacuo to give a gum which was purified by column chromatography on silica eluting with dichloromethane containing hexane (50%) then with dichloromethane containing methanol (0% up to 10%). The product-containing fractions were combined and concentrated in vacuo to give the title compound as an oil, yield 0.2 g.

Analysis %: Found: C,73.88; H,7.26; N,5.90; Calculated for C29H34N2O3.½H2O C,74.49; H,7.33; N,5.99.

¹H N.M.R. (CDCl3) δ=7.45–7.10 (m, 14H); 5.80 (brs, 1H); 5.50 (brs, 1H); 3.75 (s, 3H); 3.60 (s, 2H); 2.80–2.70 (m, 2H); 2.70–2.55 (m, 2H); 2.50–2.35 (m, 4H); 2.30 (s, 3H); 1.50–1.35 (m, 2H) ppm.

EXAMPLE 24

Preparation of 2,2-diphenyl-5-[N-methyl-N-{2-(pyridin-2-yl)ethyl}amino]pentanamide

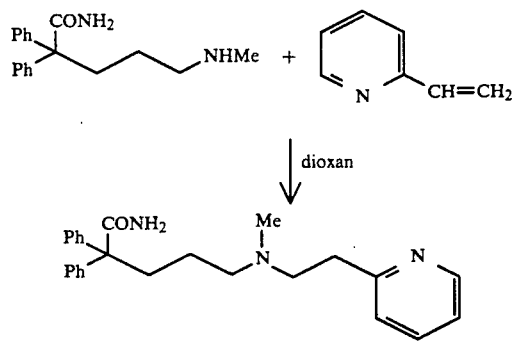

A solution containing 2,2-diphenyl-5-methylaminopentanamide (2.0 g—see Preparation 3) and 2-vinylpyridin (1.1 ml) in dioxan (15 ml) was heated under reflux for 48 hours. The mixture was concentrated in vacuo and the residue partitioned between dichloromethane (50 ml) and water (50 ml). The dichloromethane layer was dried (MgSO4) and concentrated in vacuo to give a solid which was purified by column chromatography eluting with hexane containing dichloromethane (50% up to 100%) and then with dichloromethane containing methanol (0% up to 5%). The product-containing fractions were combined and concentrated in vacuo to give the title compound as an oil which was crystallised from acetonitrile, yield 0.5 g, m.p. 134°–136°.

Analysis %: Found: C,77.22; H,7.57; N,11.05; Calculated for C25H29N3O: C,77.48; H,7.54; N,10.84.

1H N.M.R. (CDCl3) δ=8.50 (d, 1H); 7.60 (t, 1H); 7.40-7.20 (m, 10); 7.20 (d, 1H); 7.10 (m, 1H); 6.10 (brs, 1H); 5.55 (brs, 1H); 3.00-2.90 (m, 2H); 2.80-2.75 (m, 2H); 2.45-2.35 (m, 4H); 2.25 (s, 3H); 1.45-1.30 (m, 2H) ppm.

EXAMPLE 25

Preparation of 2,2-diphenyl-5-[N-(4-aminomethylphenethyl)-N-methylamino]pentanamide

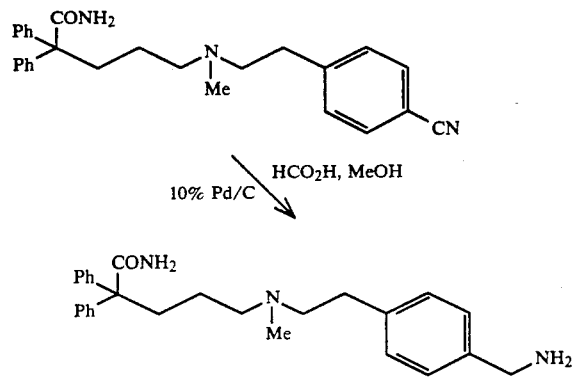

10% Palladium-on-carbon (0.3 g) was added to a solution of 2,2-diphenyl-5-[N-(4-cyanophenethyl)-N-methylamino]pentanamide (0.3 g—see Example 13) in 5% formic acid in methanol (21 ml). The mixture was stirred at room temperature under nitrogen for 1 hour, then filtered and the filtrate concentrated in vacuo to give a gum which was purified by column chromatography on silica eluting with dichloromethane containing methanol (2% up to 10%). The product-containing fractions were combined and concentrated in vacuo to give an oil which crystallised on standing. The solid was triturated with ether to give the title compound as buff crystals, yield 0.1 g, m.p. 139°-142°.

Analysis %: Found: C, 77.04; H,7.92; N,9.79; Calculated for C27H33N3O.1/15 CH2Cl2: C,76.98; H,7.90; N,9.97.

1H N.M.R. (CDCl3) δ=7.40-7.25 (m, 10H); 7.15 (ABq, 4H); 5.80 (brs, 1H); 5.45 (brs, 1H); 3.80 (s, 2H); 2.70 (m, 2H); 2.55 (m, 2H); 2.35 (m, 4H); 2.20 (s, 3H); 1.40-1.30 (m, 4H) ppm.

EXAMPLE 26

Preparation of 2,2-diphenyl-5-{N-methyl-N-2-[4-(carboxamidomethyl)phenyl]ethyl}aminopentanamide

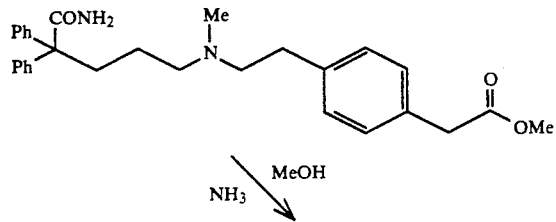

A solution of 2,2-diphenyl-5-[N-methyl-N-(4-methoxycarbonylmethylphenethyl)amino]pentanamide (0.2 g—see Example 23) in methanol (10 ml) saturated with ammonia was stirred at room temperature for 1 week. The mixture was concentrated in vacuo and the residue purified by column chromatography on silica eluting with dichloromethane containing methanol (0% up to 10%). The product-containing fractions were combined and concentrated in vacuo to give the title compound as a foam, yield 0.13 g.

Analysis %: Found: C,74.54; H,7.53; N,9.36; Calculated for C28H33N3O2.½H2O: C,74.30; H,7.32; N,8.99.

1H N.M.R. (CDCl3) δ=7.40-7.20 (m, 14H); 5.95 (brs, 1H); 5.70 (brs, 1H); 5.60 (brs, 1H); 5.40 (brs, 1H); 3.55 (s, 2H); 2.80-2.70 (m, 2H); 2.65-2.60 (m, 2H); 2.40-2.30 (m, 4H); 2.25 (s, 3H); 1.40-1.25 (m, 2H) ppm.

EXAMPLE 27

Preparation of 2,2-diphenyl-4-[N-methyl-N-(3-phenylprop-1-yl)amino]butanamide

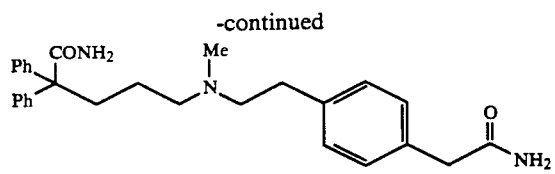

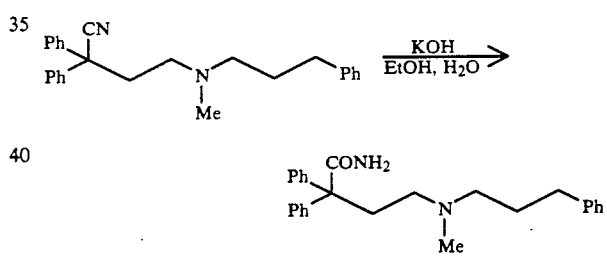

A solution of potassium hydroxide (0.2 g) in water (10 ml) was added to a solution of 1-cyano-1,1-diphenyl-3-[N-methyl-N-(3-phenylprop-I-yl)amino]propane (0.22 g—see Preparation 23) in ethanol (10 ml) and the mixture was heated at 150° C. for 20 hours in a stainless steel pressure vessel then concentrated in vacuo. Water (30 ml) was added to the residue and the mixture was extracted with dichloromethane (3×30 ml). The combined dichloromethane extracts were dried (Na2SO4) and concentrated in vacuo to give a gum which was purified by column chromatography on silica eluting with dichloromethane containing methanol (0% up to 10%). The product-containing fractions were combined and concentrated in vacuo to give the title compound as a viscous gum, yield, 0.11 g.

Analysis: Found: C,79.55; H,7.89; N,6.79; Calculated for C26H30N2O.¼ H2O:C,79.86; H,7.86; N,7.16.

1H N.M.R. (CDCl3): δ=7.40-7.15 (m, 16H); 5.70-5.60 (brs, 1H), 2.70-2.55 (m, 4H), 2.50-2.30 (m, 4H), 2.30 (s, 3H), 1.80-1.70 (m, 2H) ppm.

EXAMPLE 28

Preparation of 4-[N-(4-chlorophenethyl)-N-methylamino]-2,2-diphenylbutanamide

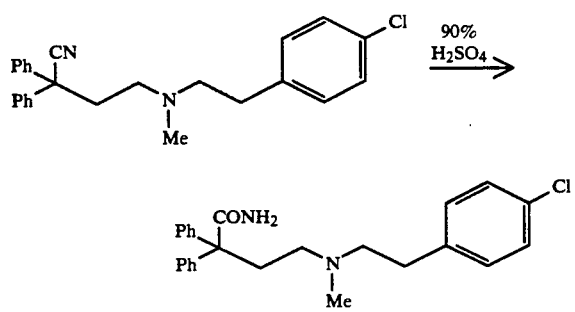

A solution of 3-[N-(4-chlorphenethyl)-N-methylamino]-1-cyano-1,1-diphenylpropane (0.2 g—Preparation 24) in 90% sulphuric acid (0.5 ml) was heated at 80°–85° c. for 3 hours. On cooling to room temperature, ice (10 g) was added and the mixture was basified (pH 10) by the addition of potassium carbonate. The mixture was extracted with dichloromethane (3×50 ml) and the combined dichloromethane extracts were washed with water (2×20 ml) then dried (Na$_2$SO$_4$) and concentrate in vacuo to give a gum. The gum was purified by column chromatography on silica eluting with hexane containing dichloromethane (25% up to 100%) followed by dichloromethane containing methanol (0% up to 5%). The product-containing fractions were combined and concentrated in vacuo to give the title compound as a gum, yield, 0.16 g.

Analysis %: Found: C,72.32; H,6.73; N,6.95; Calculated for C$_{25}$H$_{27}$ClN$_2$O.½H$_2$O: C,72.18; N,6.74.

$^1$H N.M.R. (CDCl$_3$): δ=7.40–7.25 (m, 12H); 7.15–7.05 (d, 2H), 6.90–6.70 (brs, 1H), 5.55–5.45 (brs, 1H), 2.75–2.50 (m, 5H), 2.45–2.25 (m, 3H), 2.20 (s, 3H), ppm.

EXAMPLE 29

Preparation of 2,2-diphenyl-4-[N-(4-fluorophenethyl)-M-methyl]-butanamide

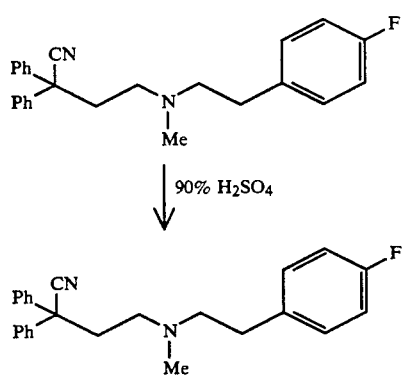

A solution of 1-cyano-1,1-diphenyl-3-[N-(4-fluorophenethyl)-N-methylamino]propane (0.4 g—see Preparation 25) in 90% sulphuric acid (1.0 ml) was heated at 95° C. for 3 hours. The mixture was poured onto ice (20 g) and basified (pH 10) by the addition of potassium carbonate. The mixture was extracted with dichloromethane (3×75 ml), the extracts were combined and then dried (Na$_2$SO$_4$) and concentrated in vacuo to give a gum. The gum was purified by column chromatography on silica eluting with hexane containing dichloromethane (25% up to 100%) and then with dichloromethane containing methanol (0% up to 5%). The product-containing fractions were combined and concentrated in vacuo to give the title compound as a viscous gum, yield, 0.25 g.

Analysis %: Found: C,75.28; H,6.90; N,7.26; Calculated for C$_{25}$H$_{27}$FN$_2$O.½H$_2$O: C,75.16; H,7.06; N,7.01.

$^1$N N.M.R. (CDCl$_3$): δ=7.45–7.25 (m, 10H), 7.15–7.10 (m, 2H), 7.05–6.95 (m, 2H), 6.90–6.70 (brs, 1H), 5.55–5.40 (brs, 1H), 2.80–2.60 (m, 6H), 2.50–2.40 (m, 2H), 2.40 (s, 3H) ppm.

EXAMPLE 30

Preparation of 1-[(5H)-5-carbamoyl-10,11-dihydrodibenzo[a,d]-cyclohepten-5-yl]-2-[N-(4-fluorophenethyl)-N-methylamino]ethane

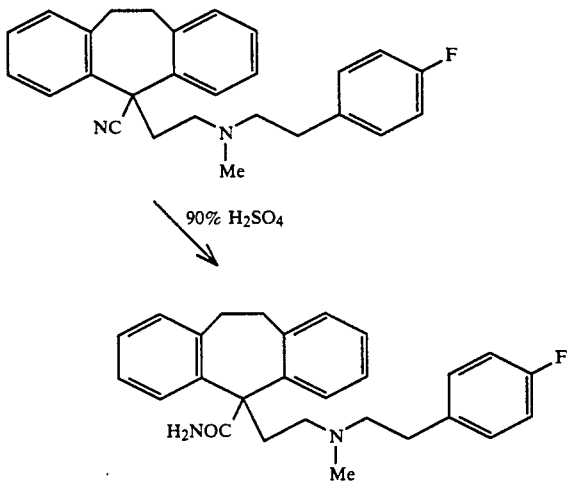

A solution of 1-[(5H)-5-cyano-10,11-dihydrodibenzo[a,d]-cyclohepten-5-yl]-2-[N-(4-fluorophenethyl-N-methylamino]ethane (0.5 g—see Preparation 27) in 90% sulphuric acid (1.0 ml) was heated at 90° C. for 30 minutes then cooled and poured onto ice (10 g). The mixture was basified (pH10) by the addition of 5N sodium hydroxide then extracted with dichloromethane (3×60 ml). The combined dichloromethane extracts were dried (Na$_2$SO$_4$) and concentrated in vacuo to give a gum which was purified by column chromatography on silica eluting with hexane containing dichloromethane (50% up to 100%) and then with dicloromethane containing methanol (0% up to 4%). The product-containing fractions were combined and concentrated in vacuo to give the title compound as a glass, yield, 0.31 g.

Analysis %: Found: C,77.35; H,6.89; N,6.78; Calculated for C$_{27}$H$_{29}$FN$_2$O: C,77.85; H,7.02; N,6.73.

$^1$H N.M.R. (CDCl$_3$): δ=7.55–7.40 (m, 2H), 7.30–6.90(m, 10H), 5.60–5.40 (brm, 2H), 3.40–3.25 (m, 2H), 3.20–3.05 (m, 2H), 2.70–2.50 (m, 6H), 2.50–2.35 (m, 2H), 2.35 (s, 3H) ppm.

EXAMPLE 31

Preparation of 4-[N-(2-{2,3-dihydrobenzofur-5yl}ethyl)-N-methylamino]-2,2-diphenylbutanamide

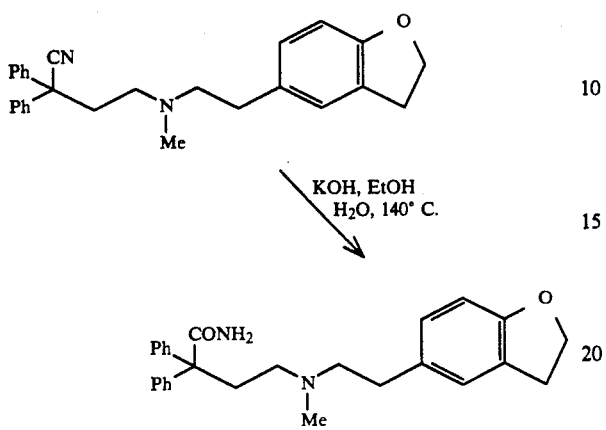

A mixture containing 1-cyano-1,1-diphenyl-3-[N-{2-(2,3-dihydrobenzofur-5-yl)ethyl}-N-methylamino]propane (0.087 g), potassium hydroxide (0.074 g), ethanol (6 ml) and water (6 ml) was heated at 140° C. in a stainless steel pressure vessel for 48 hours. On cooling to room temperature the mixture was concentrated in vacuo. Water (20 ml) was added to the residue and the mixture was extracted with dichloromethane (3×20 ml). The combined dichloromethane extracts were dried (Na$_2$SO$_4$) and concentrated in vacuo to give a gum which was purified by column chromatography on silica eluting with dichloromethane containing methanol (0% up to 10%). The product-containing fractions were combined and concentrated in vacuo to give the title compound as a glass, yield 0.056 g.

$^1$H N.M.R. (CDCl$_3$)δ=7.50–7.25 (m, 11H), 7.05 (s, 1H), 6.90–6.85 (d, 1H), 6.75–6.70 (d, 1H), 5.60–5.50 (brs, 1H), 4.65–4.50 (t, 2H), 3.25–3.15 (t, 2H), 2.95–2.65 (brm, 8H), 2.60 (brs, 3H) ppm.

Examples 32–60, in which all temperatures are in °C., illustrate the preparation of the novel starting materials used in the previous Examples:

EXAMPLE 32

Preparation of 4-bromo-1-cyano-1,1-diphenylbutane

[see also J. Med. Chem., 6, 516 (1963)]

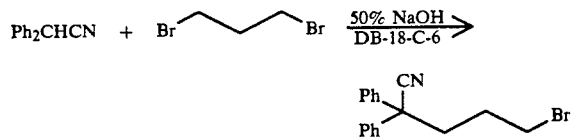

To 50% aqueous sodium hydroxide (250 ml) was added diphenyacetonitrile (30 g) followed by 1,3-dibromopropane (32 ml) and, finally, dibenzo-18-crown-6 (a phase transfer catalyst). The resulting yellow emulsion was stirred at room temperature for 1.5 hours. Toluene (200 ml) was added followed by water (50 ml). The layers were separated and the toluene solution was washed with water (50 ml) then dried (MgSO$_4$) and concentrated in vacuo. The resulting gum was crystallised from ether/hexane to give the title compound as s colourless solid, m.p. 98°–100°, yield 30 g.

$^1$H N.M.R. (CDCl$_3$)δ=7.50–7.30 (m, 10H); 3.50 (m, 2H); 2.60 (m, 2H); 2.05 (m, 2H) ppm.

EXAMPLE 33

Preparation of 4-(N-benzyl-N-methylamino)-1-cyano-1,1-diphenylbutane

[see also J. Chem. Soc., 500, (1949)]

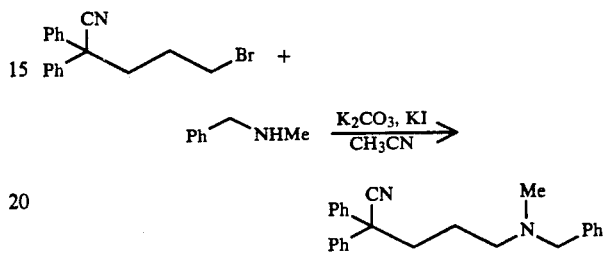

A mixture containing 4-bromo-1-cyano-1,1-diphenylbutane (25 g—see Preparation 1), N-methylbenzylamine (9.7 g), anhydrous potassium carbonate (22 g), anhydrous potassium iodide (6.6 g) and acetonitrile (250 ml) was heated under reflux for 3 hours. The mixture was concentrated in vacuo and the residue partitioned between dichloromethane (200 ml) and water (100 ml). The layers were separated and the aqueous layer extracted with dichloromethane (3×50 ml). The dichloromethane extracts were combined, dried (MgSO$_4$), and concentrated in vacuo. The resulting colourless oil was purified by column chromatography on silica gel eluting with dichloromethane containing methanol (0% up to 5%). The product-containinig fractions were combined and concentrated in vacuo. The resulting gum was crystallised from hexane/ether to give the title compound, yield 25 g, m.p. 75°–77°.

$^1$H N.M.R. (CDCl$_3$)=7.50–7.20 (m, 15H); 3.45 (s, 2H); 2.55–2.40 (m, 4H); 2.15 (s, 3H); 1.75–1.60 (m, 2H) ppm.

EXAMPLE 34

Preparation of 2,2-diphenyl-5-methylaminopentanamide

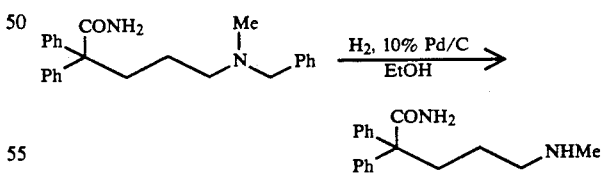

A mixture of 5-(N-benzyl-N-methylamino)-2,2-diphenylpentanamide (11 g—see Example 1) and 10% palladium-on-carbon (1.1 g) in ethanol (150 ml) was hydrogenated at room temperature and 50 p.s.i. (344.7 kPa) pressure for 87 hours. The mixture was filtered and the filtrate concentrated in vacuo to give an oil. The oil was triturated with ether to give the title compound as a colourless powder, yield 4.5 g.

$^1$H N.M.R. (CDCl$_3$)δ=7.40–7.20 (m, 11H); 5.95–5.75 (brd, 2H); 2.65–2.55 (t, 2H); 2.50–2.45 (m, 2H); 2.40 (s, 3H); 1.45–1.35 (m, 2H) ppm.

EXAMPLE 35

Preparation of 3-bromo-1-cyano-1,1-diphenylpropane

[see also J. Chem. Soc., 500, (1949)]

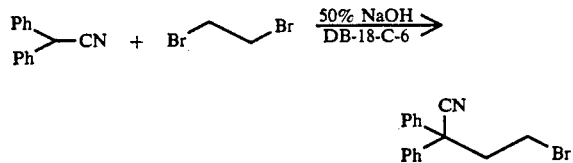

Diphenylacetonitrile (30 g) was added to 50% aqueous sodium hydroxide (250 ml) followed by 1,2-dibromomethane (27 ml) and, finally, dibenzo-18-crown-6 (0.5 g). The mixture was stirred at room temperature for 2.5 hours. Toluene (100 ml) and water (50 ml) were added, the layers separated and the aqueous layer extracted with toluene (3×50 ml). The combined toluene extracts were washed with water (100 ml) then dried (MgSO4) and concentrated in vacuo to give the title compound as a gum which was crystallised from ether/hexane, yield 34 g.

$^1$H N.M.R. (CDCl$_3$)δ7.50–7.30 (m, 10H); 3.40 (m, 2H); 3.00 (m, 2H) ppm.

EXAMPLE 36

Preparation of 3-(N-benzyl-N-methylamino)-1-cyano-1,1-diphenylpropane

[see also J. Chem. Soc., 500, (1949)]

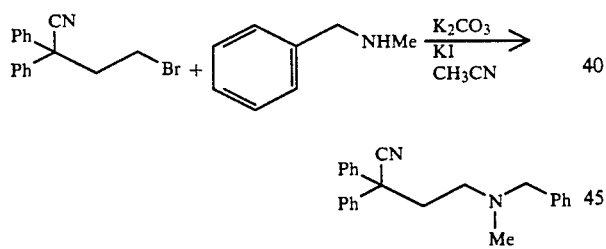

A mixture containing 3-bromo-1-cyano-1,1-diphenylpropane (24.0 g—see Preparation 4), N-methylbenzylamine (14.7 g), anhydrous potassium carbonate (22.0 g), anhydrous potassium iodide (6.6 g) and acetonitrile (250 ml) was heated under reflux for 16 hours. The mixture was concentrated in vacuo and the residue partitioned between dichloromethane (200 ml) and 10% aqueous potassium carbonate (100 ml). The layers were separated and the aqueous layer extracted with dichloromethane (3×50 ml). The combined dichloromethane extracts were dried (MgSO4) and concentrated in vacuo to give an oil which was purified by column chromatography on silica eluting with dichloromethane containing methanol (0% up to 10%). The product-containing fractions were combined and concentrated in vacuo to give the title compound as a waxy solid, yield 16.1 g.

$^1$H N.M.R. (CDCl$_3$)δ=7.45–7.25 (m, 15H); 3.5 (s, 2H); 2.70–2.50 (m, 4H); 2.25 (s, 3H) ppm.

EXAMPLE 37

Preparation of 5-(2-bromoethyl)indane

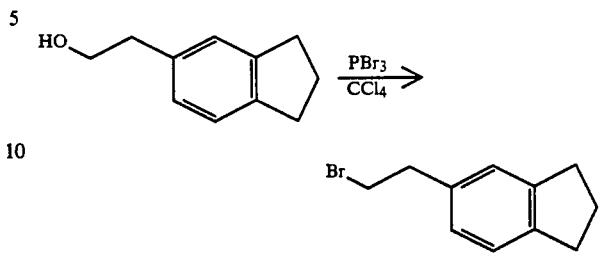

Phosphorous tribromide (3.5 ml) was added, dropwise, to a solution of 5-(2-hydroxyethyl)indane (14.0 g) (FR-A-2139628) in carbon tetrachloride (100 ml). The mixture was stirred at room temperature for 0.5 hour and then heated under reflux for 2 hours. Ice (100 g) was added and the mixture partitioned between dichloromethane and 10% aqueous sodium carbonate. The layers were separated and the aqueous layer extracted with dichloromethane (2×100 ml). The combined dichloromethane extracts were dried (MgSO4) and concentrated in vacuo to give an oil which was purified by column chromatography on silica eluting with dichloromethane. The product-containing fractions were combined and concentrated in vacuo to give the title compound as a colourless oil, yield 10.5 g.

$^1$H N.M.R. (CDCl$_3$) δ=7.30–7.00 (m, 3H); 3.60 (m, 2H); 3.20 (m, 2H; 3.00–2.85 (m, 4H); 2.20–2.05 (m, 2H) ppm.

EXAMPLE 28

Preparation of 4-chlorophenethyl bromide

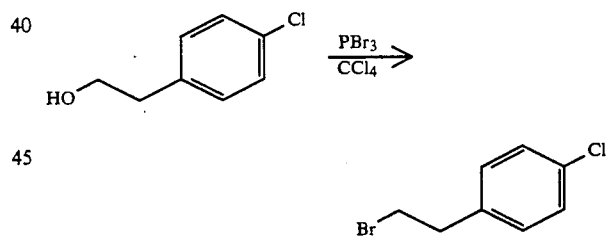

Phosphorus tribromide (1.3 ml) was added, dropwise, to a solution of 4-chlorophenethyl alcohol (5.0 g) in carbon tetrachloride (30 ml). The mixture was stirred at room temperature for 10 minutes then heated under reflux for 2 hours. Ice (50 g) was added and the mixture partitioned between dichloromethane (50 ml) and 10% aqueous sodium carbonate (50 ml). The layers were separated and the aqueous layer extracted with dichloromethane (2×50 ml). The combined dichloromethane extracts were dried (MgSO4) and concentrated in vacuo to give an oil which was purified by column chromatography on silica eluting with dichloromethane. The product-containing fractions were combined and concentrated in vacuo to give the title compound as a colourless oil, yield 3.0 g.

$^1$H N.M.R. (CDCl$_3$) δ=7.35 (d, 2H); 7.20 (d, 2H); 3.60 (t, 2E); 3.20 (t, 2H) ppm.

EXAMPLE 39

Preparation of ethyl 3-methyl-3-methylaminobutanoate

[see also J. Org. Chem., 33, 1322, (1968)]

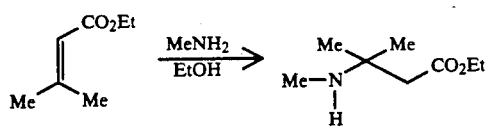

A mixture containing ethyl 3,3-dimethylacrylate (100 g) and methylamine (140 ml of a 33% solution in methylated spirit) in ethanol (400 ml) was allowed to stand at room temperature for 2 weeks. The mixture was concentrated in vacuo to give an oil which was fractionally distilled in vacuo to give the title compound as a colourless, mobile oil, yield 95.0 g. b.p. 68°-75°/20 mm.Hg.

$^1$H N.M.R. (CDCl$_3$) δ=4.1 (q, 2H); 2.40 (s, 2H); 2.30 (s, 3H); 1.60 (brs, 1H); 1.25 (t, 3H); 1.15 (s, 6H) ppm.

EXAMPLE 40

Preparation of ethyl 3-(N-benzyl-N-methylamino)-3-methylbutanoate

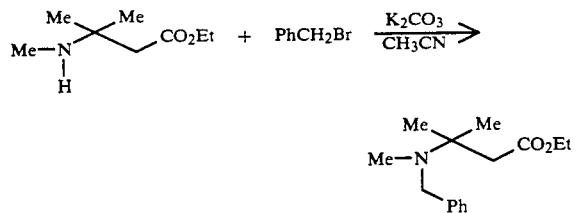

A mixture containing ethyl 3-methyl-3-methylaminobutanoate (95 g—see Preparation 8), benzyl bromide (72 ml), anhydrous potassium carbonate (138 g) and acetonitrile (500 ml) was heated under reflux for 1.5 hours. The mixture was concentrated in vacuo and the residue partitioned between dichloromethane (500 ml) and 10% aqueous potassium carbonate (300 ml). The layers were separated and the aqueous layer extracted with dichloromethane (2×100 ml). The combined dichloromethane extracts were dried (MgSO$_4$) and concentrated in vacuo to give the title compound as a mobile, colourless oil, yield 150 g.

$^1$H N.M.R. (CDCl$_3$) δ=7.40-720 (m, 5H); 4.20 (q, 2H); 3.60 (s, 2H); 2.55 (s, 2H); 2.15 (s, 3H); 1.35 (s, 6H); 1.30 (t, 3H) ppm.

EXAMPLE 41

Preparation of 3-(N-benzyl-N-methylamino)-3-methylbutan-1-ol

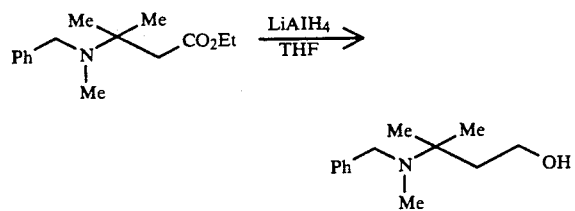

A solution of ethyl 3-(N-benzyl-N-methylamino)-3-methylbutanoate (23.6 g—see Preparation 9) in anhydrous tetrahydrofuran (100 ml) was added, dropwise, over 20 minutes to a stirred suspension of lithium aluminium hydride (7.2 g) in anhydrous tetrahydrofuran (300 ml). When the addition was complete, the mixture was stirred at room temperature for 3 hours. Water (7 ml) was carefully added dropwise followed by 15% aqueous sodium hydroxide (7 ml) and finally more water (20 ml). The resulting solid precipitate was filtered off and washed with ethyl acetate (3×50 ml). The filtrate and washings were combined and concentrated in vacuo to give the title compound as a colourless, mobile oil, yield 19.00 g.

$^1$H N.M.R. (CDCl$_3$) δ=7.40-7.20 (m, 5H); 6.15 (brs, 1H); 3.95 (t, 2H); 3.65 (s, 2H); 2.15 (s, 3H); 1.80 (t, 2H); 1.25 (s, 6H) ppm.

EXAMPLE 42

Preparation of 2-(N-benzyl-N-methylamino)-4-chloro-2methylbutane hydrochloride

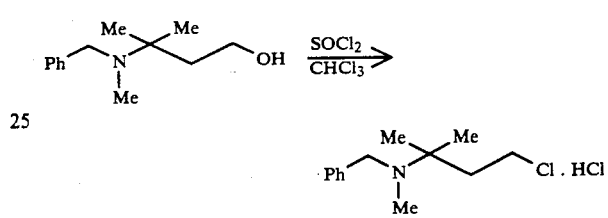

A solution of 3-(N-benzyl-N-methylamino)-3-methylbutan-1-ol (6.9 g—see Preparation 10) in chloroform (20 ml) was added dropwise over 30 minutes to a solution of thionyl chloride (4.9 ml) in chloroform (20ml) at 0°. When the addition was complete, the mixture was stirred at room temperature for 18 hours. Ethanol (5 ml) was added and the mixture concentrated in vacuo to give an oil which was crystallised from ethyl acetate to give the title compound as a colourless powder, yield 2.62 g, m.p. 164°-166°.

$^1$H N.M.R. (CDCl$_3$) δ=7.75 (m, 2H); 7.50-7.40 (m, 3H); 4.70 (dd, 1H); 3.80-3.65 (m, 3H); 2.60-2.45 (m, 5H); 1.70 (d, 6H) ppm.

EXAMPLE 43

Preparation of 4-(n-benzyl-N-methylamino)-1-cyano-1,1-diphenyl-4-methylpentane

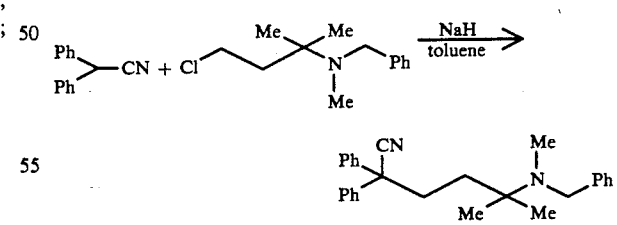

Sodium hydride (4.4 g of a 60% dispersion in mineral oil) was added in portions to a solution of diphenylacetonitrile (19.3 g) in anhydrous toluene (100 ml). The mixture was heated under reflux for 1.5 hours then allowed to cool to 50° whereupon a solution of 2-(N-benzyl-N-methylamino)-4-chloro-2-methylbutane (11.3 g—see Preparation 11) in anhydrous toluene (20 ml) was added and the mixture heated under reflux for 3 hours. The mixture was partitioned between toluene (200 ml) and 10% aqueous sodium hydroxide (100 ml), the layers separated and the toluene layer washed with water (100 ml). The toluene solution was dried (MgSO₄) and concentrated in vacuo to five an oil which was purified by column chromatography on silica eluting with hexane containing toluene (50% up to 100%) and then with toluene containing ethyl acetate (0% up to 10%). The product-containing fractions were combined and concentrated in vacuo to give the title compound as a straw coloured oil, yield 14.5 g.

¹H N.M.R. (CDCl₃) δ=7.50-7.20 (m, 15H); 3.45 (s, 2H); 2.70-2.60 (m, 2H); 2.05 (s, 3H); 1.70-1.60 (m, 2H); 1.15 (s, 6H) ppm.

EXAMPLE 44

Preparation of 2,2-diphenyl-5methyl-5-methylaminohexanamide

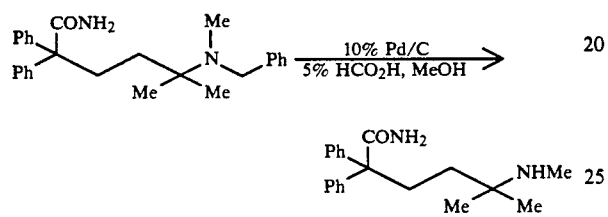

10% Palladium-on-carbon was added to a solution of 5-(N-benzyl-N-methylamino)-2,2-diphenyl-5-methylhexanamide (0.6 g—see Example 3) in methanol (19 ml) and formic acid (1 ml). The mixture was stirred at room temperature for 16 hours then filtered and the filtrate concentrated in vacuo to give the title compound as a gum, yield 0.4 g.

¹H N.M.R. (CDCl₃) δ=7.40-7.25 (m, 11H); 6.85 (brs, 1H); 5.90
(brs, 1H); 2.55-2.45 (m, 2H); 2.30 (s, 3H); 1.40 (m, 2H); 1.20 (s,
3H) ppm.

EXAMPLE 45

3,4-Methylenedioxyphenethyl alcohol

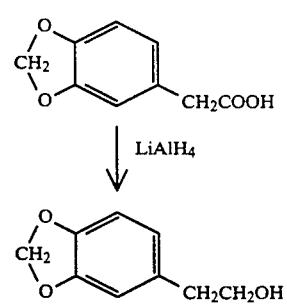

3,4-Methylenedioxyphenylacetic acid (18.0 g) was added portionwise over 30 minutes to a stirred, ice-cooled suspension of lithium aluminium hydride (4.0 g) in ether (400 ml) and the mixture was stirred at room temperature for two hours, quenched by the cautious addition of saturated aqueous ammonium chloride solution and filtered. The filtrate was washed with 10% aqueous sodium carbonate solution, dried over magnesium sulphate and evaporated to give the title compound as a pale yellow oil (15.01 g, 90%), which was characterised by its ¹H-n.m.r. spectrum.

¹H N.M.R. (CDCl₃) δ=6.69-6.83 (3H, m); 5.98 (2H, s); 3.82 (2H, dt, J=7 and 6 Hz); 2.81 (2H, t, J=7 Hz) and 1.44 (1H, t, j=6 Hz, exchangeable with D₂O).

EXAMPLE 46

3,4-Methylenedioxyphenethyl bromide

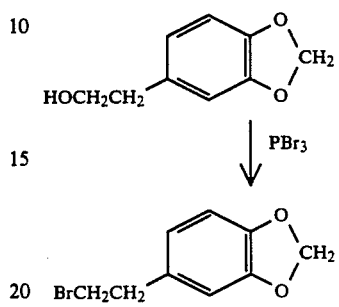

A solution of phosphorus tribromide (8.1 g) in carbon tetrachloride (50 ml) was added dropwise over 30 minutes to a stirred solution of 3,4-methylenedioxyphenethyl alcohol (15.0 g) (see Preparation 14) in carbon tetrachloride (200 ml) and the mixture was heated under reflux for 3 hours, washed sequentially with water (twice), 5M aqueous sodium hydroxide solution and water, dried over magnesium sulphate and evaporated. The residue was purified by chromatography on silica (100 g) using carbon tetrachloride as the eluant. Appropriate fractions were combined and evaporated to give the title compound as a pale yellow oil (8.3 g, 40%), which was characterised by its ¹H-n.m.r. spectrum.

¹H N.M.R. (CDCl₃) δ=6.80 (1H, d, j=8 Hz), 6.75 (1H, s); 6.71 (1H, d, j=8 Hz); 6.00 (2H, s); 3.56 (2H, t, j=7 Hz) and 3.13 (2H, t, J=7Hz).

EXAMPLE 47

6-(2-Hydroxyethyl)benzodioxan

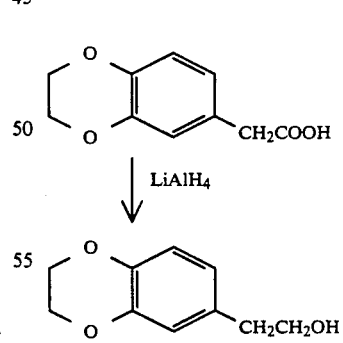

This prepared as described in Preparation 14 using (benzodioxan-6-yl)acetic acid instead of 3,4-methylenedioxyphenylacetic acid. The title compound was obtained as a colourless oil (19.8 g, 92%), which was characterised by its ¹H-n.m.r. spectrum.

¹H N.M.R. (CDCl₃) δ=6.84 (1H, d, j=8 Hz); 6.77 (1H, d, j=2 Hz); 6.73 (1H, dd, j=8 and 2 Hz); 4.28 (4H, s); 3.59 (2H, t, j=7 Hz) and 3.08 (2H, t, j=7 Hz).

EXAMPLE 48

6-(2-Bromoethyl)benzodioxan

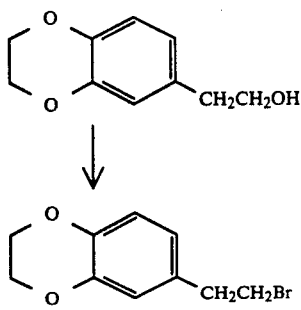

This was prepared as described in Preparation 15 using 6-(2-hydroxyethyl)benzodioxan (see Preparation 16) instead of 3,4-methylenedioxyphenethyl alcohol. The title compound was obtained as a pale yellow oil (21.4 g, 80%), which was characterised by its $^1$H-N.M.R. spectrum.

$^1$H-N.M.R. (CDCl$_3$) δ=6.83 (1H, d, J=8 Hz); 6.77 (1H, d, J=2 Hz); 6.72 (1H, dd, J=8 and 2 Hz); (4H, s); 3.59 (2H, t, J=7 Hz) and 3.10 (2H, t, J=7 Hz).

EXAMPLE 49

N-[4-(2-methanesulphonyloxyethyl)phenyl]methanesulphonamide

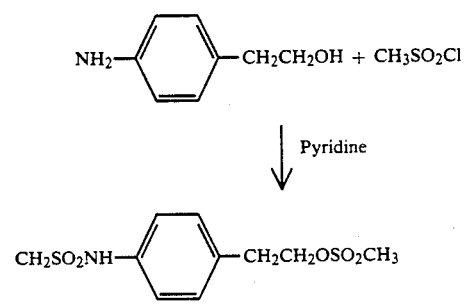

Methanesulphonyl chloride (50.4 g) was added dropwise to a stirred solution of 4-aminophenethyl alcohol (27.44 g) in dry pyridine (300 ml) at 0° and the solution was stirred at 0° for 30 minutes and then at room temperature for 2.5 hours. It was then poured into water and the solid was filtered off, washed with water, dried and crystallised from ethyl acetate to give the title compound (39.0 g, 66%), m.p. 136°-137°.

Analysis %: Found: C,40.6; H,5.2; N4.9; C$_{10}$H$_{15}$NO$_5$S$_2$ requires: C,40.9; H,5.1; N,4.8.

EXAMPLE 50

Preparation of 5-(2-hydroxyethyl)-2,3-dihydrobenzofuran

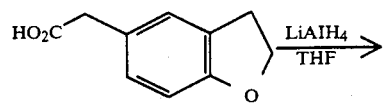

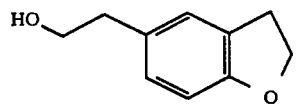

A solution of (2,3-dihydrobenzofuran-5-yl)acetic acid (4.9 g—see EP-A-132130) in anhydrous tetrahydrofuran (50 ml) was added over 10 minutes, dropwise, to a stirred suspension of lithium aluminum hydride (1.57 g) in anhydrous tetrahydrofuran (50 ml) at 0°. The mixture was allowed to warm to room temperature and stirred for 1 hour. Water (1.5 ml) was then added dropwise with caution followed by 10% aqueous sodium hydroxide (1.5 ml) and, finally, water (4.5 ml). The mixture was filtered and the inorganic salts washed with ethyl acetate (2×50 ml). The filtrate and washings were combined and concentrateed in vacuo to give the title compound as an oil, yield 3.3 g.

$^1$H N.M.R. (CDCl$_3$) δ=7.10 (s, 1H; 7.00 (d, 1H); 6.75 (m, 1H); 4.65–4.55 (m, 2H); 3.90–3.75 (m, 2H); 3.30–3.15 (m, 2H); 2.90–2.80 (m, 2H); 1.85–1.75 (brs, 1H) ppm.

EXAMPLE 51

Preparation of 5-(2-bromoethyl)-2,3-dihydrobenzofuran

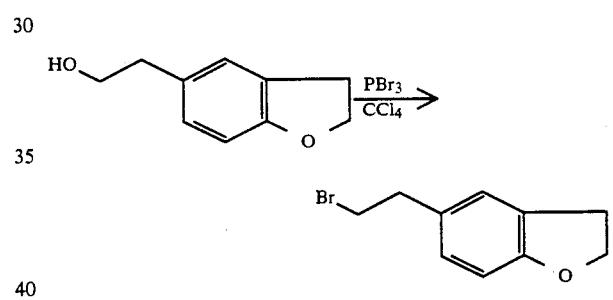

Phosphorus tribromide (0.37 g) was added to a solution of 5-(2-hydroxyethyl)-2,3-dihydrobenzofuran (0.612 g—see Preparation 19) in carbon tetrachloride (3 ml) and the mixture heated under reflux for 3 hours. On cooling to room temperature, the mixture was partitioned between 10% aqueous sodium carbonate (20 ml) and dichloromethane (20 ml). The layers were separated and the aqueous layer extracted with dichloromethane (3×10 ml). The combined dichloromethane extracts were dried (MgSO$_4$) and concentrated in vacuo to give the title compound as an oil which crystallised on standing, yield 0.584 g, m.p. 60°-62°.

$^1$H N.M.R. (CDCl$_3$) δ=7.10 (s, 1H); 7.00–6.95 (d, 1H); 6.80–6.70 (d, 1H); 4.65–4.55 (t, 2H); 3.60–3.50 (t, 2H); 3.25–3.15 l(t, 2H); 3.15–3.10 (t, 2H) ppm.

EXAMPLE 52

Preparation of methyl 4-(2-hydroxyethyl)phenylacetate

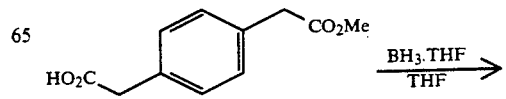

-continued

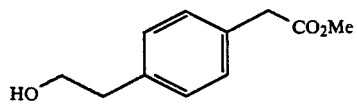

Borane-tetrahydrofuran complex (40 ml of a 1.0 molar solution in tetrahydrofuran) was added, dropwise over 10 minutes, to a solution of 4-(methoxycarbonyl-methyl)phenylacetic acid (see U.S. Pat. No. 3,341,531) (7.7 g) in tetrahydrofuran (100 ml) at 0°. The mixture was allowed to warm to room temperature and stirred for 2 hours. The reaction was quenched by the addition of 2M hydrochloric acid (50 ml) then concentrated in vacuo. The residue was partitioned between dichloromethane (200 ml) and 2M hydrochloric acid (100 ml), the layers separated, and the aqueous layer extracted with dichloromethane (2×50 ml). The combined dichloromethane extracts were dried (MgSO₄) and concentrated in vacuo to give an oil which was dissolved in ethyl acetate (100 ml) and the solution extracted with saturated aqueous sodium bicarbonate (2×100 ml). The aqueous extracts were combined, acidified with 2M hydrochloric acid (pH5) and extracted with dichloromethane (2×100 ml). The combined dichloromethane extracts were dried (MgSO₄) and concentrated in vacuo to give the title compound as an oil, yield 2.7 g.

$^1$H N.M.R. (CDCl₃) δ=7.30–7.10 (m, 4H); 3.90–3.80 (m, 2H); 3.70 (s, 3H); 2.95–2.85 (m, 2H) ppm.

EXAMPLE 53

Preparation of methyl 4-(2-bromoethyl)phenylacetate

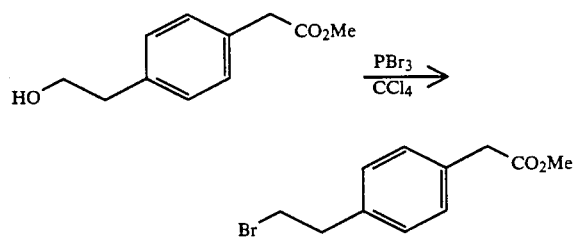

Phosphorus tribromide (1.42 g) was added, dropwise, to a solution of methyl 4-(2-hydroxyethyl)phenylacetate (2.7 g—see Preparation 21) in carbon tetrachloride (20 ml) at 0°. When the addition was complete, the mixture was allowed to warm to room temperature and then heated under reflux for 2 hours. Ice (100 g) was added and the mixture was partitioned between dichloromethane (50 ml) and saturated aqueous sodium bicarbonate (50 ml). The layers were separated and the aqueous layer extracted with dichloromethane (3×50 ml). The combined dichloromethane extracts were dried (MgSO₄) and concentrated in vacuo to give an oil which was purified by column chromatography on silica eluting with dichloromethane containing hexane (40%) then with dichloromethane. The product-containing fractions were combined and concentrated in vacuo to give the title compound as an oil, yield 1.02 g.

$^1$H N.M.R. (CDCl₃) δ=7.30–7.20 (m, 4H); 3.75 (s, 3H); 3.65 (s, 2H); 3.65–3.55 (m, 2H); 3.25–3.15 (m, 2H) ppm.

EXAMPLE 54

Preparation of 1-cyano-1,1-diphenyl-3-[N-methyl-N(3-phenylprop-1-yl)amino]propane

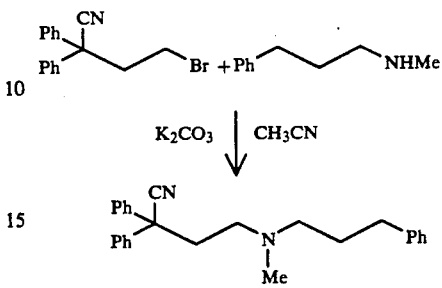

A mixture containing 3-bromo-1-cyano-1,1-diphenylpropane (1.5 g—see Preparation 4), 1-(N-methylamino)-3-phenylpropane (0.746 g), anhydrous potassium carbonate (1.38 g) and acetonitrile (50 ml) was heated under reflux for 48 hours and then concentrated in vacuo. Water (30 ml) was added to the residue and the mixture was extracted with dichloromethane (3×40 ml). The combined dichloromethane extracts were dried (Na₂SO₄) and concentrated in vacuo to give a gum which was purified by column chromatography on silica eluting with hexane containing dichloromethane (25% up to 100%) and then dichloromethane containing methanol (0% up to 4%). The product-containing fractions were combined and concentrated in vacuo to give the title compound as a gum, yield, 0.93 g.

Analysis %: Found: C,84.87; H,7.99; N,7.76; Calculated for $C_{26}H_{28}N_2$: C,84.74; H,7.66; N,7.60.

$^1$H N.M.R. (CDCl₃) δ=7.50–7.15 (m, 15H), 2.70–2.45 (m, 6H), 2.45–2.30 (m, 2H), 2.25 (s, 3H), 1.80–1.70 (m, 2H) ppm.

EXAMPLE 55

Preparation of 3-[N-(4-chlorophenethyl)-N-methylamino]-1-cyano-1,1-diphenylpropane

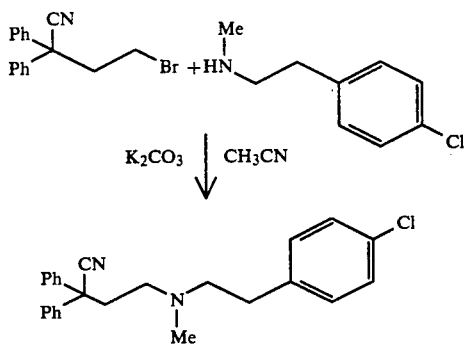

A mixture containing 3-bromo-1-cyano-1,1-diphenylpropane (0.9 g—see Preparation 4), N-methyl-4-chlorophenethylamine (0.51 g, see CA 61:15224h), anhydrous potassium carbonate (0.83 g) and acetonitrile (40 ml) was heated under reflux for 24 hours then partitioned between dichloromethane (50 ml) and water (50 ml). The dichloromethane layer was dried (Na₂SO₄) and concentrated in vacuo to give a gum which was purified by column chromatography on silica eluting with hexane containing dichloromethane (25% up to 40%) and then with dichloromethane containing methanol (0% up to 5%). The product-containing fractions were combined and concentrated in vacuo to give the title compound as a gum yield, 0.25 g.

Analysis %: Found: C,75.06; H,6.44; N,7.07; Calculated for C$_{25}$H$_{25}$ClN$_2$.½H$_2$O: C,75.45; H,6.59; N,7.04.

$^1$H N.M.R. (CDCl$_3$): δ=7.50–7.25 (m, 12H), 7.15–7.05 (d, 2H), 2.75–2.50 (m, 8H), 2.35 (s, 3H) ppm.

EXAMPLE 56

Preparation of 1-cyano-1,1-diphenyl-3-[N-(4-fluorophenethyl)-N-methylamino]propane

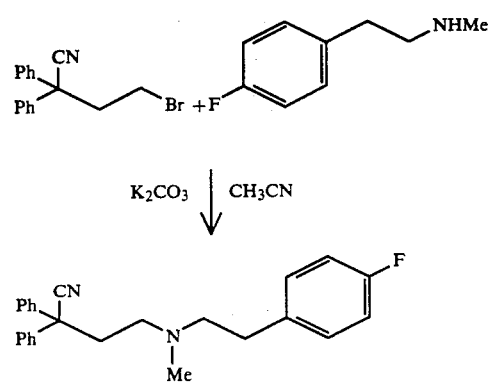

A mixture containing 3-bromo-1-cyano-1,1-diphenylpropane (1.5 g)—see Preparation 4), N-methyl-4-fluorophenethylamine (0.766 g—see CA 80:P1Z0985y), anhydrous potassium carbonate (1.38 g) and acetonitrile (50 ml) was heated under reflux for 24 hours then concentrated in vacuo. The residue was dissolved in water (40 ml) and extracted with dichloromethane (3×50 ml). The combined dichloromethane extracts were dried (Na$_2$SO$_4$) and concentrated in vacuo to give a gum which was purified by column chromatography on silica eluting with hexane containing dichloromethane (25% up to 100%) and then with dichloromethane containing methanol (0% up to 3%). The product-containing fractions were combined and concentrated in vacuo to give the title compound as a gum, yield, 0.51 g.

Analysis: Found: C,80.40; H,6.78; N,7.95; Calculated for C$_{25}$H$_{25}$FN$_2$: C,80.61; H,6.77; N,7.52.

$^1$H N.M.R. (CDCl$_3$) δ=7.45–7.30 (m, 10H), 7.15–7.10 (m, 2H), 7.05–6.95 (m, 2H), 2.75–2.65 (m, 2H), 2.65–2.50 (m, 6H), 2.35 ) s, 3H) ppm.

EXAMPLE 57

Preparation of 1-[(5H)-5-cyano-10,11-dihydrodibenzo[a,d]-cyclohepten-5-yl]-2-bromoethane

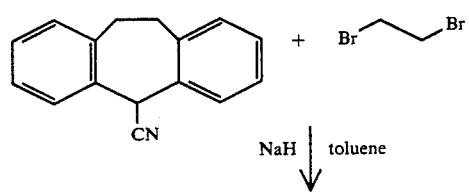

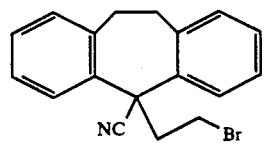

A solution of (5H)-5-cyano-10,11-dihydrodibenzo[a,d]cycloheptene]11.0 g —see J. Med. Chem., 6, 254, (1963)] in anhydrous toluene (50 ml) was added dropwise, under a nitrogen atmosphere, to a stirred suspension of sodium hydride (1.65 g of an 80% dispersion in mineral oil) in toluene (50 ml). When the addition was complete, the mixture was heated under reflux for 2.5 hours. The mixture was cooled to 10° C. whereupon a solution of 1,2-dibromoethane (18.8 g) in toluene (10 ml) was added dropwise and then heated under reflux for 4 hours. On cooling the mixture to room temperature, water (60 ml) was added and the layers separated. The aqueous layer was extracted with ethyl acetate (100 ml), the organic layers were combined then dried (Na$_2$SO$_4$) and concentrated in vacuo to give a viscous gum. The gum was purified by distillation to give the title compound as a straw-coloured oil, yield, 8.5 g, b.p. 188°–192° C./0.3 mm Hg.

$^1$H N.M.R. (CDCl$_3$): δ=8.05–7.95 (m, 2H), 7.40–7.20 (m, 6H), 3.50–3.30 (m, 2H), 3.25–3.15 (m, 2H), 3.15–3.00 (m, 4H) ppm.

EXAMPLE 58

Preparation of 1-[(5-cyano-10,11-dihydrodibenzo[a,d]cyclohepten-5-yl]-2-[N-(4-fluorophenethyl)-N-methylamino]ethane

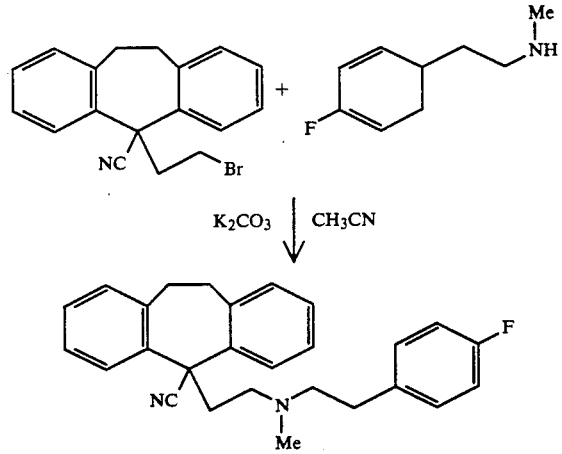

A mixture containing 1-[(5-cyano-10,11-dihydrodibenzo[a,d]cyclohepten-5-yl]-2-bromoethane (3.26 g — see Preparation 26), N-methyl-4-fluorophenethylamine (1.53 g — see C.A. 80:P120985y), anhydrous potassium carbonate (2.76 g) and acetonitrile (50 ml) was heated under reflux for 24 hours then concentrated in vacuo. Water (50 ml) was added to the residue and the resulting mixture was extracted with dichloromethane (3×60 ml). The combined dichloromethane extracts were dried (Na$_2$SO$_4$) and concentrated in vacuo to give an oil which was purified by column chromatography on silica eluting with hexane containing dichloromethane (25% up to 100%) and then with dichloromethane containing methanol (0% up to 5%). The product-containing fractions were combined and concentrated in vacuo to give the title compound as a viscous oil, yield, 1.7 g.

Analysis %: Found: C,81.11; H,6.79; N,6.76; Calculated for $C_{27}H_{27}FN_2$: C,81.37; H,6.83; N,7.03.

$^1$H N.M.R. (CDCl$_3$) δ=8.00-7.90 (m, 2H), 7.30-6.90 (m, 10H), 3.50-3.35 (m, 2H), 3.15-3.05 (m, 2H), 2.70-2.55 (m, 4H), 2.22-2.45 (m, 2H), 2.45-2.30 (m, 2H), 2.25 (m, 3H) ppm.

EXAMPLE 59

Preparation of
N-{2-(2,3-dihydrobenzofuran-5-yl)ethyl} methylamine

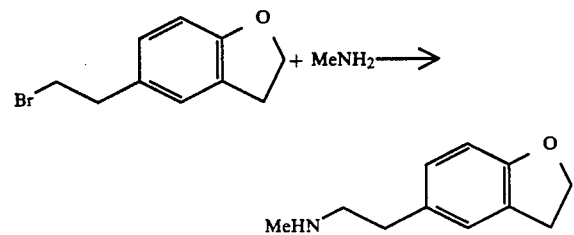

A solution of 5-(2-bromoethyl)-2,3-dihydrobenzofuran (1.5 g — see Preparation 20) in 33% methylamine in methanol (40 ml) was heated at 100° C. in a stainless steel pressure vessel for 6 hours then concentrated in vacuo. The residue was partitioned between dichloromethane (50 ml) and 10% aqueous sodium carbonate (50 ml). The layers were separated and the aqueous layer was further extracted with dichloromethane (2×50 ml). The aqueous layer was concentrated in vacuo to give a solid which was triturated with boiling 2-propanol. The mixture was filtered and the filtrate concentrated in vacuo to give a solid which was purified by column chromatography o silica eluting with dichloromethane containing methanol (0% up to 1%). The product-containing fractions were combined and concentrated in vacuo to give the title compound as a colourless solid, yield, 0.31 g, m.p. 153°-155° C.

$^1$H N.M.R. (CDCl$_3$) δ=9.80-9.60 (brs, 1H), 7.10 (s, 1H), 7.00-6.95
(d, 1H), 6.75-6.70 (d, 1H), 4.60-4.50 (t, 2H), 3.30-3.10 (m, 6H), 2.75 (s, 3H) ppm.

EXAMPLE 60

Preparation of
1-cyano-1,1-diphenyl-3-[N-{2-(2,3-dihydrobenzofur-5-yl)ethyl}-N-methylamino]propane

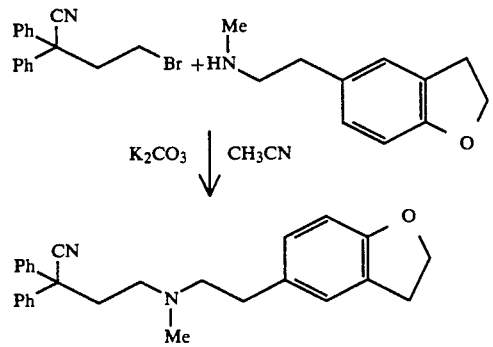

A mixture containing 3-bromo-1-cyano-1,1-diphenylpropane (0.3 g — see Preparation 4), N-[2-(2,3-dihydrobenzofur-5-yl) ethyl]-N-methylamine (0.177 g — see Preparation 28), anhydrous potassium carbonate (0.276 g) and acetonitrile (25 ml) was heated under reflux for 48 hours. On cooling to room temperature, the mixture was concentrated in vacuo and the residue was partitioned between water (20 ml) and dichloromethane (40 ml). The layers were separated and the aqueous layer further extracted with dichloromethane (2×20 ml). The combined dichloromethane extracts were dried (Na$_2$SO$_4$) and concentrated in vacuo to give an oil which was purified by column chromatography on silica eluting with hexane containing dichloromethane (50% up to 100%) and then with dichloromethane containing methanol (0% up to 5%). The product-containing fractions were combined and concentrated in vacuo to give the title compound as an oil, yield, 0.13 g.

Analysis %:
Found: C,81.58; H,7.20; N,7.23; Calculated for $C_{27}H_{28}H_2O$: C,81.78; H,7.12; N,7.07.

$^1$H N.M.R. (CDCl$_3$) δ=7.50-7.30 (m, 10H), 7.05 (s, 1H), 6.95-6.90 (d, 1H), 6.75-6.70(d, 1H), 4.65-4.55 (t, 2H), 3.25-3.15 (t, 2H), 2.70-2.50 (m, 8H), 2.35 (s, 3H) ppm.

We claim:
1. A compound of the formula

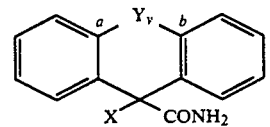

or a pharmaceutically acceptable salt thereof, wherein
v is 0 or 1, and when v is 0, there is no bond between the carbons at positions a and b;
Y is —CH$_2$CH$_2$—, —CH=CH—, —CH$_2$—S—, —CH$_2$—O—, —O— or —S—; and X is a group of the formula:

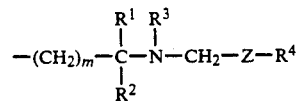

wherein
m is 1 or 2;
$R^1$ and $R^2$ are each independently H or $C_1$-$C_4$ alkyl, or $R^1$ and $R^2$ together represent —(CH$_2$)$_n$— wherein n is an integer of from 2 to 5;
$R^3$ is H or $C_1$-$C_4$ alkyl;
Z is a direct link, —CH$_2$—, —(CH$_2$)$_2$—, —CH$_2$O— or —CH$_2$S—; and
$R^4$ is pyridyl, pyrazinyl, thienyl or a group of the formula

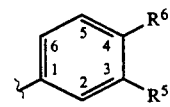

wherein
either $R^5$ and $R^6$ are each independently selected from H, $C_1$-$C_4$ alkyl, $C_1$-$C_4$ alkoxy, halo, —CF$_3$, —CN, —(CH$_2$)$_p$NR$^7$R$^8$, —OCO($C_1$-$C_4$ alkyl), —CO($C_1$-$C_4$ alkyl), —CH(OH) ($C_1$-$C_4$ alkyl), —C(OH) ($C_1$-$C_4$ alkyl)$_2$, —SO$_2$NH$_2$, —NHSO$_2$(-$C_1$-$C_4$ alkyl), —(CH$_2$)$_p$OH, —(CH$_2$)$_p$COO($C_1$-$C_4$ alkyl), and —(CH$_2$)$_p$CONR$^7$R$^8$, or R$^5$ and R$^6$ together represent —(CH$_2$)$_q$—, —O (CH$_2$)$_r$O— wherein one oxygen atom is attached to the 3-position of the benzene ring and the other is attached to the 4-position, or —O(CH$_2$)$_r$— wherein the oxygen atom is attached to the 3- or 4- position of the benzene ring;

R$^7$ and R$^8$ are each independently H or C$_1$-C$_4$ alkyl;

p is 0, 1 or 2;

q is 3, 4 or 5;

r is 1, 2 or 3; and t is 2, 3 or 4;

with the proviso that when v is zero and z is —CH$_2$—, —(CH$_2$)$_2$— or a direct link, R$^4$ must be pyridyl, pyrazinyl or thienyl.

2. A compound as claimed in claim 1 wherein R$^1$ and R$^2$ are either both H or both CH$_3$.

3. A compound according to claim 1 wherein R$^3$ is CH$_3$.

4. A compound as claimed in claim 1 wherein Z is a direct link, CH$_2$ or (CH$_2$)$_2$.

5. A compound as claimed in 1 wherein R$^4$ is either pyridyl, or a group of the formula:

where either one of R$^5$ and R$^6$ is H and the other is H, C$_1$-C$_4$ alkyl, hydroxy, C$_1$-C$_4$ alkoxy, hydroxymethyl, halo, cyano, carbamoyl, carbamoylmethyl, sulphamoyl, C$_1$-C$_4$ alkanesulphonamido, (C$_1$-C$_4$ alkoxycarbonyl)-methyl or aminomethyl, or R$^5$ and R$^6$ together represent —(CH$_2$)$_3$—, —OCH$_2$O—, —O(CH$_2$)$_2$O— or —O(CH$_2$)$_2$—.

6. A compound as claimed in claim 5 wherein R$^4$ is a group of the formula:

7. A compound as claimed in claim 1, wherein v is 0.

8. A compound as claimed in any one of claims 1, wherein v is 1 and Y is —CH$_2$CH$_2$—.

9. A compound according to claim 1 having the chemical name 2,2-diphenyl-5-[N- 2-(indan-5-yl)-ethyl-N-methylamino]pentanamide, 2,2-diphenyl-5-[N- 2-(2,3-dihydrobenzofur-5-yl)ethyl -N-methylamino]pentanamide or 4-[N-(4-chlorophenethyl)-N-methylamino]-2,2-diphenylbutanamide.

10. A compound as claimed in claim 1 wherein Z is a direct link, —CH$_2$—, —CH$_2$O— or —CH$_2$S—.

11. A pharmaceutical composition for treating or preventing a disease associated with the altered motility or tone of smooth muscle in a mammal in need thereof, comprising a compound as claimed in claim 1, and a pharmaceutically acceptable carrier.

12. A method of preventing a disease associated with the altered motility or tone of smooth muscle in a mammal in need thereof, comprising administering to said mammal an amount of a compound according to the formula

I or pharmaceutically acceptable salt thereof, wherein v is 0 or 1, and when v is 0, there is no bond between the carbons at positions a and b;

Y is —CH$_2$CH$_2$—, —CH=CH—, —CH$_2$—S—, —CH$_2$—O—, —O— or —S—; and

X is a group of the formula:

wherein m is 1 or 2;

R$^1$ and R$^2$ are each independently H or (C$_1$-C$_4$)alkyl, or R$^1$ and R$^2$ together represent —(CH$_2$)$_n$— wherein n is an integer or from 2 to 5;

R$^3$ is H or (C$_1$-C$_4$)alkyl;

Z is a direct link, —CH$_2$—, —(CH$_2$)$_2$—, —CH$_2$O— or —CH$_2$S—; and R$^4$ is pyridyl, pyrazinyl, thienyl or a group of the formula wherein either R$^5$ and R$^6$ are each independently selected from H, (C$_1$-C$_4$)alkyl, (C$_1$-C$_4$)alkoxy, halo, —CF$_3$, —CN, —(CH$_2$)$_p$NR$^7$R$^8$, —OCO(C$_1$-C$_4$)alkyl, —CO(C$_1$-C$_4$)alkyl, —CH(OH) (C$_1$-C$_4$)alkyl, —C(OH)-di(C$_1$-C$_4$)alkyl, —SO$_2$NH$_2$, —NHSO$_2$(-C$_1$-C$_4$)alkyl, —(CH$_2$)$_p$OH, —(CH$_2$)$_p$COO(C$_1$-C$_4$)alkyl and, (CH$_2$)$_p$CONR$^7$R$^8$, or R$^5$ and R$^6$ together represent —(CH$_2$)$_q$—, —O(CH$_2$)$_r$O— wherein one oxygen atom is attached to the 3-position of the benzene ring and the other is attached to the 4-position, or —O(CH$_2$)$_r$— wherein the oxygen atom is attached to the 3- or 4- position of the benzene ring;

R$^7$ and R$^8$ are each independently 8 or (C$_1$-C$_4$)alkyl;

p is 0, 1 or 2;

q is 3, 4 or 5;

r is 1, 2 or 3; and t is 2, 3 or 4;

effective in alleviating or preventing such disease.

* * * * *